(12) United States Patent
Kim et al.

(10) Patent No.: US 8,639,447 B2
(45) Date of Patent: Jan. 28, 2014

(54) METHOD FOR IDENTIFYING PEPTIDES USING TANDEM MASS SPECTRA BY DYNAMICALLY DETERMINING THE NUMBER OF PEPTIDE RECONSTRUCTIONS REQUIRED

(75) Inventors: Sangtae Kim, San Diego, CA (US); Nitin Gupta, La Jolla, CA (US); Pavel A. Pevzner, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 783 days.

(21) Appl. No.: 12/602,481

(22) PCT Filed: Jun. 2, 2008

(86) PCT No.: PCT/US2008/065548
§ 371 (c)(1),
(2), (4) Date: Nov. 30, 2009

(87) PCT Pub. No.: WO2008/151140
PCT Pub. Date: Dec. 11, 2008

(65) Prior Publication Data
US 2010/0179766 A1  Jul. 15, 2010

Related U.S. Application Data

(60) Provisional application No. 60/941,276, filed on May 31, 2007.

(51) Int. Cl.
*G01N 33/48* (2006.01)
*G01N 31/00* (2006.01)
*G06F 7/60* (2006.01)
*G06F 19/22* (2011.01)
*G06F 19/12* (2011.01)

(52) U.S. Cl.
CPC ............... *G06F 19/22* (2013.01); *G06F 19/12* (2013.01)
USPC ................................. 702/19; 702/22; 703/2

(58) Field of Classification Search
None
See application file for complete search history.

(56) References Cited

U.S. PATENT DOCUMENTS

2007/0224704 A1   9/2007   Gordon et al.

FOREIGN PATENT DOCUMENTS

| JP | 2006-58111 | 3/2006 |
|---|---|---|
| KR | 10-0531207 | 11/2005 |
| KR | 10-2007-0017676 | 2/2007 |

OTHER PUBLICATIONS

Frank et al. Peptide sequence tags for fast database search in mass-spectrometry. Journal of Proteome Research, 2005, vol. 4, pp. 1287-1295.*

(Continued)

*Primary Examiner* — Russell S Negin
(74) *Attorney, Agent, or Firm* — Eleanor M. Musick; Procopio, Cory, Hargreaves & Savitch LLP

(57) ABSTRACT

A method for identifying peptides using tandem mass spectrometry takes the spectrum for a peptide to be analyzed and uses a scoring function to score a match between the spectrum and each candidate peptide in a peptide database. The scoring function has a value corresponding to a number of fragment peaks in the spectrum that match fragment peaks in a spectrum of the candidate peptide. Using the match scores, a generating function of the spectrum is computed to determine the number of peptide reconstructions at each value of the scoring function. The generating function is then used to determine the number of candidate peptides for each match score and the probability of a peptide having a given match score to the spectrum. A spectral probability can be determined by calculating the total probability of all peptides with scores equal to or larger than the given match score.

7 Claims, 19 Drawing Sheets

(56) References Cited

OTHER PUBLICATIONS

Dancik et al. De novo peptide sequencing vai tandem mass spectrometry. Journal of Computational Biology, 1999, vol. 6, pp. 327-342.*

International Search Report and Written Opinion issued Jan. 21, 2009 in PCT/US2008/065548.

* cited by examiner

| # explained b & y peaks (X) | # peptides with X explained b & y peaks (E(S,X)) |
|---|---|
| 13 | 360 |
| 12 | 12940 |
| 11* | 146836 |
| 10 | 1166509 |
| 9 | 6946516 |
| 8 | 35080724 |
| 7 | 149410781 |
| 6 | 550113802 |
| 5** | 1735636721 |

Energy=2 (spans rows 13, 12, 11*)
Delta=6 (spans rows 11* through 5**)

\* Highest score of a database peptide
\*\* Second highest score of a database peptide

FIG. 2b

| Score (X) | # Peptides with score X | Probability of peptides with score X | Spectral Probability for score X | |
|---|---|---|---|---|
| 64 | 24 | 3.20E-11 | 3.20E-11 | |
| 63 | 200 | 2.25E-10 | 2.57E-10 | |
| 62 | 16 | 7.81E-14 | 2.57E-10 | Energy=4 |
| 61 | 24 | 4.30E-14 | 2.57E-10 | |
| 60* | 42 | 1.86E-11 | 2.76E-10 | |
| 59 | 510 | 1.36E-10 | 4.12E-10 | |
| 58 | 604 | 7.51E-11 | 4.87E-10 | |
| 57 | 316 | 3.04E-10 | 7.91E-10 | |
| 56 | 686 | 4.35E-10 | 1.23E-09 | |
| 55 | 956 | 4.30E-10 | 1.66E-09 | |
| 54 | 1648 | 5.33E-10 | 2.19E-09 | |
| 53 | 1759 | 9.40E-10 | 3.13E-09 | |
| 52 | 3299 | 6.56E-10 | 3.79E-09 | |
| 51 | 2996 | 5.15E-10 | 4.30E-09 | |
| 50 | 4902 | 2.02E-09 | 6.33E-09 | |
| 49 | 5486 | 1.27E-09 | 7.60E-09 | |
| 48 | 7571 | 1.67E-09 | 9.27E-09 | |
| 47 | 11772 | 4.64E-09 | 1.39E-08 | |
| 46 | 12275 | 4.37E-09 | 1.83E-08 | |
| 45 | 17312 | 5.03E-09 | 2.33E-08 | |
| 44 | 18546 | 5.13E-09 | 2.84E-08 | |
| 43 | 29686 | 9.03E-09 | 3.75E-08 | |
| 42 | 35984 | 9.89E-09 | 4.74E-08 | |
| 41 | 43537 | 9.66E-09 | 5.70E-08 | Delta=33 |
| 40 | 51089 | 1.31E-08 | 7.01E-08 | |
| 39 | 68199 | 2.16E-08 | 9.17E-08 | |
| 38 | 92724 | 2.34E-08 | 1.15E-07 | |
| 37 | 101464 | 2.95E-08 | 1.45E-07 | |
| 36 | 197710 | 3.84E-08 | 1.83E-07 | |
| 35 | 215618 | 5.23E-08 | 2.35E-07 | |
| 34 | 279465 | 7.47E-08 | 3.10E-07 | |
| 33 | 317856 | 8.32E-08 | 3.93E-07 | |
| 32 | 398058 | 8.68E-08 | 4.80E-07 | |
| 31 | 496905 | 1.32E-07 | 6.12E-07 | |
| 30 | 562972 | 1.36E-07 | 7.49E-07 | |
| 29 | 729187 | 1.81E-07 | 9.29E-07 | |
| 28 | 852838 | 2.04E-07 | 1.13E-06 | |
| 27** | 1016310 | 2.43E-07 | 1.38E-06 | |
| 26 | 1181540 | 3.18E-07 | 1.69E-06 | |
| 25 | 1450134 | 2.97E-07 | 1.99E-06 | |

FIG. 2c

| Rank | b | y | b-H2O | y-H2O | b-NH3 | y-NH3 | a | b+1 | y+1 | b++ | y++ |
|---|---|---|---|---|---|---|---|---|---|---|---|
| 1.00 | 2.28 | 4.76 | -1.61 | 0.00 | 0.69 | 0.18 | 0.00 | 0.47 | -0.51 | 3.77 | 2.45 |
| 2.00 | 3.67 | 4.45 | -0.09 | 1.16 | 0.31 | 0.92 | 2.70 | -0.09 | 2.95 | 3.32 | 2.98 |
| 3.00 | 3.77 | 4.10 | 0.46 | 1.09 | -0.01 | 0.58 | 2.37 | 1.27 | 3.19 | 2.70 | 2.27 |
| 4.00 | 3.84 | 4.17 | 0.74 | 1.26 | 0.16 | 1.03 | 3.07 | 1.26 | 3.63 | 2.98 | 2.86 |
| 5.00 | 3.52 | 4.09 | 1.10 | 1.89 | 1.46 | 0.41 | 2.79 | 1.29 | 3.37 | 2.93 | 2.33 |
| 6.00 | 3.54 | 4.19 | 1.32 | 1.44 | 1.54 | 0.85 | 2.50 | 1.84 | 3.33 | 2.85 | 2.67 |
| 7.00 | 3.91 | 4.35 | 1.52 | 2.21 | 1.81 | 1.01 | 2.60 | 2.11 | 3.53 | 2.78 | 2.64 |
| 8.00 | 3.60 | 3.91 | 1.60 | 2.20 | 1.77 | 1.15 | 2.53 | 2.12 | 3.07 | 2.53 | 2.17 |
| 9.00 | 3.58 | 3.90 | 1.42 | 1.86 | 1.95 | 1.06 | 2.14 | 1.98 | 3.20 | 2.06 | 2.11 |
| 10.00 | 3.76 | 3.98 | 1.92 | 2.24 | 1.76 | 0.83 | 2.37 | 2.41 | 3.31 | 2.24 | 2.18 |
| ... | ... | ... | ... | ... | ... | ... | ... | ... | ... | ... | ... |
| 151.00 | -1.09 | -1.58 | -0.45 | -0.63 | -0.43 | -0.59 | -0.44 | -0.80 | -1.03 | -0.18 | -0.26 |

FIG. 9a

| Rank | b | y | b-H2O | y-H2O | b-NH3 | y-NH3 | a | b+1 | y+1 | b++ | y++ |
|---|---|---|---|---|---|---|---|---|---|---|---|
| 1.00 | 2.02 | 4.46 | -0.16 | -0.16 | 0.16 | 0.25 | 0.33 | -0.04 | -0.45 | 3.48 | 2.69 |
| 2.00 | 2.94 | 4.28 | 0.16 | 0.63 | 0.16 | 0.49 | 1.52 | 0.56 | 2.98 | 3.14 | 2.59 |
| 3.00 | 3.53 | 4.21 | 0.10 | 0.20 | 0.47 | 0.30 | 2.12 | 0.79 | 2.88 | 2.83 | 2.48 |
| 4.00 | 3.45 | 3.83 | 0.52 | 0.58 | 0.14 | 0.63 | 2.33 | 1.21 | 2.82 | 2.63 | 2.43 |
| 5.00 | 3.46 | 4.03 | 0.83 | 0.88 | 1.11 | 0.28 | 2.58 | 1.78 | 3.00 | 2.52 | 2.33 |
| 6.00 | 3.47 | 4.10 | 1.02 | 1.06 | 1.15 | 0.17 | 2.13 | 1.44 | 3.09 | 2.56 | 2.47 |
| 7.00 | 3.44 | 3.85 | 1.10 | 1.21 | 1.06 | 0.65 | 2.02 | 1.64 | 3.10 | 2.08 | 2.41 |
| 8.00 | 3.68 | 3.84 | 1.59 | 1.32 | 1.51 | 0.44 | 2.18 | 1.74 | 2.93 | 2.20 | 2.40 |
| 9.00 | 3.62 | 3.71 | 1.91 | 1.05 | 1.63 | 0.80 | 2.06 | 1.77 | 3.12 | 1.95 | 2.31 |
| 10.00 | 3.63 | 3.71 | 1.69 | 1.41 | 1.41 | 1.02 | 1.87 | 1.76 | 3.28 | 1.67 | 2.32 |
| ... | ... | ... | ... | ... | ... | ... | ... | ... | ... | ... | ... |
| 151.00 | -1.15 | -1.58 | -0.47 | -0.46 | -0.43 | -0.42 | -0.38 | -0.75 | -0.94 | -0.15 | -0.26 |

FIG. 9b

| Rank | b | y | b-H2O | y-H2O | b-NH3 | y-NH3 | a | b+1 | y+1 | b++ | y++ |
|---|---|---|---|---|---|---|---|---|---|---|---|
| 1.00 | 2.20 | 4.17 | -0.51 | -0.92 | -0.51 | -0.92 | 0.00 | 0.69 | 1.10 | 0.79 | 2.18 |
| 2.00 | 2.89 | 4.18 | 0.69 | -0.56 | 0.13 | -0.56 | -0.15 | 1.74 | 3.31 | 0.13 | 1.97 |
| 3.00 | 2.75 | 4.18 | 1.71 | -0.14 | 0.71 | 0.37 | -0.54 | 1.71 | 3.07 | -0.14 | 2.10 |
| 4.00 | 2.88 | 4.02 | 0.68 | -0.17 | 1.30 | -0.58 | -0.17 | 2.17 | 3.16 | 0.68 | 1.73 |
| 5.00 | 2.79 | 3.82 | 0.90 | 0.55 | 1.24 | -0.01 | -0.30 | 1.60 | 3.13 | 1.24 | 1.60 |
| 6.00 | 2.96 | 3.98 | 1.93 | 0.99 | 1.50 | -0.11 | 0.59 | 1.89 | 3.32 | 1.28 | 1.63 |
| 7.00 | 2.65 | 3.67 | 0.99 | 0.12 | 1.28 | 0.30 | -0.39 | 1.94 | 3.04 | 0.45 | 1.50 |
| 8.00 | 2.72 | 3.72 | 1.62 | 0.24 | 1.27 | 0.57 | 0.93 | 1.85 | 3.02 | 1.03 | 1.76 |
| 9.00 | 3.16 | 4.01 | 2.49 | 0.41 | 1.85 | 0.63 | 1.22 | 2.28 | 3.56 | 0.97 | 1.79 |
| 10.00 | 2.96 | 3.75 | 1.74 | 0.18 | 1.28 | 0.59 | 0.59 | 2.16 | 3.26 | 0.59 | 1.89 |
| ... | ... | ... | ... | ... | ... | ... | ... | ... | ... | ... | ... |
| 151.00 | -0.69 | -0.94 | -0.32 | -0.14 | -0.28 | -0.15 | -0.05 | -0.42 | -0.64 | -0.05 | -0.14 |

FIG. 9c

METHOD FOR IDENTIFYING PEPTIDES USING TANDEM MASS SPECTRA BY DYNAMICALLY DETERMINING THE NUMBER OF PEPTIDE RECONSTRUCTIONS REQUIRED

RELATED APPLICATIONS

This application claims the priority of U.S. Provisional Application No. 60/941,276, filed May 31, 2007, which is incorporated herein by reference.

GOVERNMENT RIGHTS

This invention was made with government support under 1-R01-RR16522 awarded by the National Institute of General Medical Sciences (NIGMS), the National Institutes of Health. The government has certain rights in the invention.

BACKGROUND OF THE INVENTION

Tandem mass spectrometry (MS/MS) has become the leading high-throughput technology for protein identification. A tandem mass spectrometer is capable of ionizing a mixture of peptides with different sequences and measuring their respective parent mass/charge ratios, selectively fragmenting each peptide into pieces and measuring the mass/charge ratios of the fragment ions. Thus, a tandem mass spectrum can be viewed as a collection of fragment masses from a single peptide. This set of mass values is a "fingerprint" that identifies the peptide. The peptide sequencing problem is then to derive the sequence of the peptides given their MS/MS spectra. For an ideal fragmentation process and an ideal mass spectrometer, the sequence of a peptide could be easily determined by converting the mass differences of the consecutive ions in a spectrum to the corresponding amino acids. This ideal situation would occur if the fragmentation process could be controlled so that each peptide was cleaved between every two consecutive amino acids and a single charge was retained on only the N-terminal piece. In practice, however, the fragmentation processes in mass spectrometers are far from ideal.

The problem for tandem mass spectrometry peptide sequencing is, given a spectrum S, the ion types $\Delta$, and the mass m, find a peptide of mass m with the maximal match to spectrum S. Peptide fragmentation in a tandem mass spectrometer can be characterized by a set of numbers $\Delta = \{\delta_1, \ldots, \delta_k\}$ representing ion types. A $\delta$-ion of a partial peptide $P' \subset P$ is a modification of P' that has mass m(P')-$\delta$. For tandem mass spectrometry, the theoretical spectrum of peptide P can be calculated by subtracting all possible ion types $\{\delta_1, \ldots, \delta_k\}$ from the masses of all partial peptides of P (i.e., every partial peptide generates k masses in the theoretical spectrum.) An (experimental) spectrum $S=\{s_1, \ldots, s_m\}$ is a set of masses of fragment ions. A match between spectrum S and peptide P is the number of masses that experimental and theoretical spectra have in common.

Recent progress in mass spectrometry instrumentation has produced LTQ-FT mass spectrometers that can generate on the order of 100,000 spectra per day per machine. Software is a significant and limiting factor in mass spectrometry proteomics analysis—typical large datasets may require days or weeks of computational time on expensive computers or grids.

Most peptide identification algorithms use database search methods that match the spectra against a protein database. Existing database search methods in mass spectrometry, such as SEQUEST (U.S. Pat. No. 6,017,693, which is incorporated herein by reference) and MASCOT, match spectra against a sequence database to identify the peptides. FIG. 1 illustrates an exemplary process for a spectrum matching techniques for peptide identification. Specifically, a sample 12 is provided to a tandem mass spectrometer 14. A two-step process is illustrated, however, single step processes are also known. In the first mass spectrometer, a peptide ion is selected, so that a targeted component of a specific mass is separated from the rest of the sample 14a. The targeted component is then activated or decomposed. In the case of a peptide, the result will be a mixture of the ionized parent peptide ("precursor ion") and component peptides of lower mass which are ionized to various states. A number of activation methods can be used including collisions with neutral gases (also referred to as collision induced dissolution). The parent peptide and its fragments are then provided to the second mass spectrometer 14c, which outputs an intensity and m/z for each of the plurality of fragments in the fragment mixture. This information can be output as a fragment mass spectrum 16. In the spectrum 16, each fragment ion is represented as a bar graph whose abscissa value indicates the mass-to-charge ratio (m/z) and whose ordinate value represents intensity. In the process, sub-sequences contained in the protein sequence library 20 are used as a basis for predicting a plurality of mass spectra 22. The predicted mass spectra 22 of the sub-sequences are compared 24 to the experimentally-derived fragment spectrum 16 to identify one or more of the predicted mass spectra which most closely match the experimentally-derived fragment spectrum 16. A report containing one or more of the matching "potential" sub-sequences are output to a monitor, printer, or other viewing means 28 and/or the data is stored in a storage medium 26 for subsequent retrieval for further processing or viewing.

While these spectrum matching tools are invaluable, they are too slow for matching large MS/MS datasets against large protein databases. Since SEQUEST compares every spectrum against every database peptide, it would take a cluster of about 60 processors to analyze in real time the spectra produced by one of the newer mass-spectrometers (if searching through the Swiss-Prot database). If one were to attempt to perform a time-consuming search for post-translational modifications, the running time may further increase by orders of magnitude. One of the major problems in tandem mass spectrometry is the lack of a concrete theoretical probability model, thus requiring searching of the spectrum against a random decoy (negative control) database to empirically estimate the error rates (often represented by Poisson, Gaussian, hypergeometric, or other approximations of tails of score distributions) as opposed to the analytically derived and database-independent error rates in genomics tools such as BLAST. In fact, the Proteomics Publication Guidelines recommend searching in decoy databases to determine the statistical significance of peptide identifications. The rationale behind using a decoy database is to estimate the number of spectra that match the database by chance. If a spectrum S has probability p(S) of matching a random database, then a decoy database is simply a time-consuming way to evaluate $\Sigma p(S)$ over all spectra in the dataset. This sum represents the expected number of hits in the decoy database but is not a good way to estimate individual probabilities p(S).

From one perspective, use of decoy databases can be seen as an acknowledgment of an inability to solve the following problem: Given a spectrum S and a score threshold T for a spectrum-peptide scoring function, find the probability that a random peptide matches the spectrum S with score equal to or larger than T.

One proposed solution to this Spectrum Matching Problem takes a heuristic approach based on approximating the tail of the score distribution. Solving the Spectrum Matching Problem is equivalent to computing the False Positive Rates (FPR) of spectral matches. FPR is a property of an individual spectrum as opposed to the False Discovery Rate (FDR), which is the property of multiple spectra (proportion of incorrect identifications among all identifications judged correct).

Search in a decoy database appears to be an attractive approach for approximating the solution of the Spectrum Matching Problem as m/n, where m is the number of matches between the spectrum and the decoy database of size n (with scores equal to or larger than the threshold T). However, for an individual spectrum, the number of matches for typical n is usually zero, thus making this approach problematic (decoy and target databases usually have the same size). To obtain reliable FPR for an individual spectrum, one can increase n (e.g., making giant decoy databases 1000 times larger than target databases). Since this is impractical, some existing approaches bundle all spectra with the same score to evaluate the FDR of all spectra in the bundle and to use FDR as a surrogate for FPR. However, this approach can be a dangerous oversimplification because spectra with the same score may have vastly different FPRs, thus suggesting that careful analysis of all peaks in the spectrum (rather than the scores alone) may be necessary to compute the database matching statistics for individual spectra.

Although the target-decoy search strategy is currently viewed as the best way to distinguish between the correct and false identifications, this approach has a number of shortcomings, not the least of which is the effective doubling of the search time.

In addition to the complications resulting from the use of decoy databases, another problem with current methods is that a protein database is not always available, for example, when the samples are derived from an organism with an unknown proteome. In these cases, de novo peptide sequencing algorithms are required.

De novo peptide sequencing represents a fast alternative to MS/MS database search. While the best de novo algorithms are orders of magnitude faster than the fastest database search tools (even on moderately sized databases), they are less accurate. However, the superior accuracy of the database search tools becomes less pronounced with the increase in the database size. Thus, searches in very large databases represent an important niche where de novo based approaches are more accurate and orders of magnitude faster than the traditional database search approaches.

A number of de novo methods have been developed, including Lutefisk, SHERENGA, PepNovo, PEAKS, EigenMS, NovoHMM and PILOT. A commonly used technique in de novo methods is the spectrum graph approach, where a spectrum is represented as a graph with peaks as vertices that are connected by edges if their mass difference corresponds to the mass of an amino acid. The vertices of the spectrum graph are further scored based on peak intensities and neutral losses, and a peptide sequence is obtained by finding a longest path in the graph. This has been achieved using diverse optimization methods including branch and bound search (Lutefisk), dynamic programming (SHERENGA, PEAKS, PepNovo, NovoHMM), spring models (EigenMS), and integer programming (PILOT).

De novo peptide sequencing can be viewed as a search in the database of all possible peptides. Even if this time consuming search were feasible, it would remain unclear which peptide in the database of all peptides represents the actual peptide that generated the spectrum. It is estimated that in about half of the cases, the existing database search tools will fail to identify the correct peptide since its score will be lower than the score of an incorrect peptide. For a typical spectrum identified in a database search, there may be hundreds, and even thousands, of very different peptides that "explain" the spectrum better. As a result, any de novo peptide sequencing algorithm should output multiple peptide reconstructions rather than a single reconstruction. Matching these peptides against a database results in a hybrid de novo based database search that bypasses the time-consuming matching of spectra against the database.

Similar to generating the covering set of tags (that in most applications limited to tags of length 3), one can attempt to generate the covering sets of full length peptide reconstructions that with high probability contain the correct peptide, i.e., a "spectral dictionary". Spectral dictionaries take the peptide sequence tag approach one step further by generating peptide reconstructions and ensuring that one of them is correct. They also have the potential to improve the filtration efficiency of tag based tools, for example, the filtration efficiency of 1000 de novo reconstructions of length 10 is orders of magnitude higher than even a single tag of length 3. However, while spectral dictionaries have important advantages over spectral tags, generating them remains an open problem.

Spectral dictionaries may have an edge over the traditional MS/MS approaches in searching very large databases, e.g., six-frame translations of entire genomes. Various proteogenomic studies have demonstrated that MS/MS search against a six frame translation of the genome allows one to use MS/MS data for finding new genes, predicting programmed frame shifts, correcting DNA sequencing errors, etc. However, existing MS/MS database search tools are impractical for searches against the six-frame translation of large genomes such as the human genome (~3 billion amino acids after removing repeats). Indeed, most early proteogenomic studies were limited to searches against the 6-frame translations of bacterial genomes. The largest proteogenomic analysis conducted so far was the search against the 6-frame translation of *Arabidopsis thaliana*, which resulted in the discovery of nearly 400 new genes using InsPecT. However, InsPecT cannot be scaled to search the 20-times larger 6-frame translation of the human genome.

Spectral dictionaries make the size of the database almost irrelevant since the spectral dictionary can be matched against the six-frame translation as efficiently as against a much smaller database of known proteins. Since many genes remain unidentified even in the well studied organisms, the searches in six-frame translation represent a valuable tool for proteogenomic annotations. Spectral dictionaries are also helpful in searches for fusion peptides that are common in tumor proteomes but not explicitly present in protein databases.

Spectral dictionaries allow every MS/MS database search tool to be turned into a de novo peptide sequencing software (by simply running this tool on all peptides from the spectral dictionary and selecting the top scoring peptide). After such "conversion", it may be possible to estimate how well both database search tools and de novo tools would perform on very large databases. This experiment, however, yields a disappointing performance of both de novo and database search tools: only 35% to 42% of peptides of length 10 were correctly reconstructed in such experiments (35%, 38%, and 42% for X!Tandem, PepNovo, and InsPecT, respectively).

The key unsolved problem is how many reconstructions must be generated to avoid losing the correct peptide. Generating too few peptides will lead to false negative errors while generating too many peptides will lead to false positive errors. Some de novo algorithms output a single or a fixed number (decided before the search) of peptides. For some spectra, generating only one reconstruction may be enough to guarantee finding the correct peptide while in other cases (even with the same parent mass), a thousand reconstructions may be insufficient.

The problem of generating varying numbers of reconstructions for each spectrum becomes particularly important for long peptides with the increasing complexity of the search space. For example, the accuracy of PepNovo (i.e., the percentage of correctly reconstructed amino acids) falls sharply with increase in the peptide length, from 89% for length 7 to 50% for length 20 peptides. As a result, PepNovo correctly reconstructs 59% of peptides of length 7 and only 8% of peptides of length 20.

A recently disclosed method addressed de novo peptide sequencing for data acquired from FT-ICR instruments when both the parent mass and the peak positions are accurate. However, acquiring such spectra can be expensive and time-consuming. An intermediate approach is to acquire mass spectra with high precision at MS1 stage and lower precision at MS/MS stage, giving accurate parent mass but inaccurate peak positions. However, the existing de novo search methods are aimed toward low accuracy ion trap mass spectrometers that have parent mass errors on the order of 1 Dalton. Since vertices in the spectrum graph are constructed based on low accuracy peaks, it is not clear in these algorithms how to exploit the accurate parent mass information that is available from new high accuracy instruments. In other words, it is not clear how to incorporate "high accuracy parent mass/low accuracy MS/MS spectrum" data into the existing de novo approaches.

In view of the numerous shortcomings of existing methods, the need remains for faster and more accurate methods for interpreting tandem mass spectra for peptide identification. The present invention is directed to such methods.

SUMMARY OF THE INVENTION

According to the present invention, an algorithm is provided for determining the statistical significance in a spectrum matching approach of identified peptides directly based on the spectrum and peptide sequence, without reference to a decoy database. This is done by computing the generating function of the spectrum, i.e., the number of peptide reconstructions at each value of a scoring function, to provide a technique referred to as mass-spectrometry-generating function, or "MS-GF". The inventive method allows identification of statistically-significant peptide reconstructions without resort to time-consuming decoy database searches, thereby reducing the database search time by nearly half relative to existing peptide identification tools.

In one aspect, the inventive method for identifying peptides using tandem mass spectrometry involves the steps of: obtaining a spectrum for a peptide to be analyzed, the spectrum comprising a plurality of fragment peaks and having a parent mass, each fragment peak corresponding to a mass within the spectrum; using a scoring function, scoring a match between the spectrum and each candidate peptide of a plurality of candidate peptides to generate a match score for each candidate peptide, wherein the scoring function has a value corresponding to a number of fragment peaks in the spectrum matching fragment peaks in a spectrum of the candidate peptide; using the match scores, computing a generating function of the spectrum to determine a number of peptide reconstructions at each value of the scoring function; determining a score distribution of match scores of all candidate peptides for the spectrum; and generating an output to a display device comprising a listing of the score distribution for the spectrum according to the number of fragment peaks. In further steps, the number of candidate peptides for each match score and the probability of a peptide having a given match score can be determined. A spectral probability can be determined by calculating the total probability of all peptides with scores equal to or larger than the given match score. These values allow optimization of the number of candidate peptides that should be considered for analysis of a spectrum of an unknown peptide, providing a significant improvement over prior art methods.

In another aspect, the invention allows an estimate of the appropriate number of peptide reconstructions to be reported in a peptide identification algorithm, thus increasing the likelihood of finding the correct peptide without excessive false positives. By reporting an appropriate number of peptide reconstructions for each spectrum, the invention enables an effective hybrid peptide identification algorithm, using de novo peptide reconstructions for database searching.

In still another aspect, the invention enables accurate peptide identification when parent mass is accurate even if the peak positions are not accurate.

Spectral dictionaries can be searched efficiently against a protein database resulting in a new approach to peptide identification. For the success of this approach, it is critical to generate a small set of spectral dictionaries that with high probability contains the correct peptide. The de novo approach according to the present invention fits into this hybrid scheme by generating the appropriate number of peptide reconstructions for each spectrum.

According to the present invention, the spectrum is represented as an amino-acid graph with a vertex for each integer between 0 and M·|S| where |S| represents the parent mass of the spectrum, and M is a multiplication factor for higher resolution (more than one Da). Vertices corresponding to the peaks in the spectrum are assigned values equal to the rank of the peak. To accommodate low accuracy peaks, all vertices within a threshold distance are also assigned the same value as the vertex with the peak. Vertices whose distance corresponds to an amino acid mass are connected by an edge. Dynamic programming can then be used to compute the number of peptide reconstructions of mass i and score t represented by S(i,t) for all values of i and t.

The inventive algorithm provides the accurate number of peptide reconstructions corresponding to a specified statistical significance. It is capable of improving the sensitivity/specificity trade off in a database search, as well as useful for building a de-novo based database search tool for peptide identification.

BRIEF DESCRIPTION OF THE DRAWINGS

FIGS. 2a-2c illustrate the generating function according to the present invention, where FIG. 2a shows a spectrum S of peptide GAIDKAEEIR; FIG. 2b is a table listing the number of peptides (E(S, X)) that explain X b/y peaks in this spectrum; and FIG. 2c is a table listing the result of a uniformly weighted generating function of the same spectrum.

FIGS. 9a-9c are three tables of scores for matching different ion types with a peak of different lengths (7 (FIG. 9a), 8 (FIG. 9b) and 20 (FIG. 9c), respectively).

DETAILED DESCRIPTION OF THE INVENTION

Figure 1:
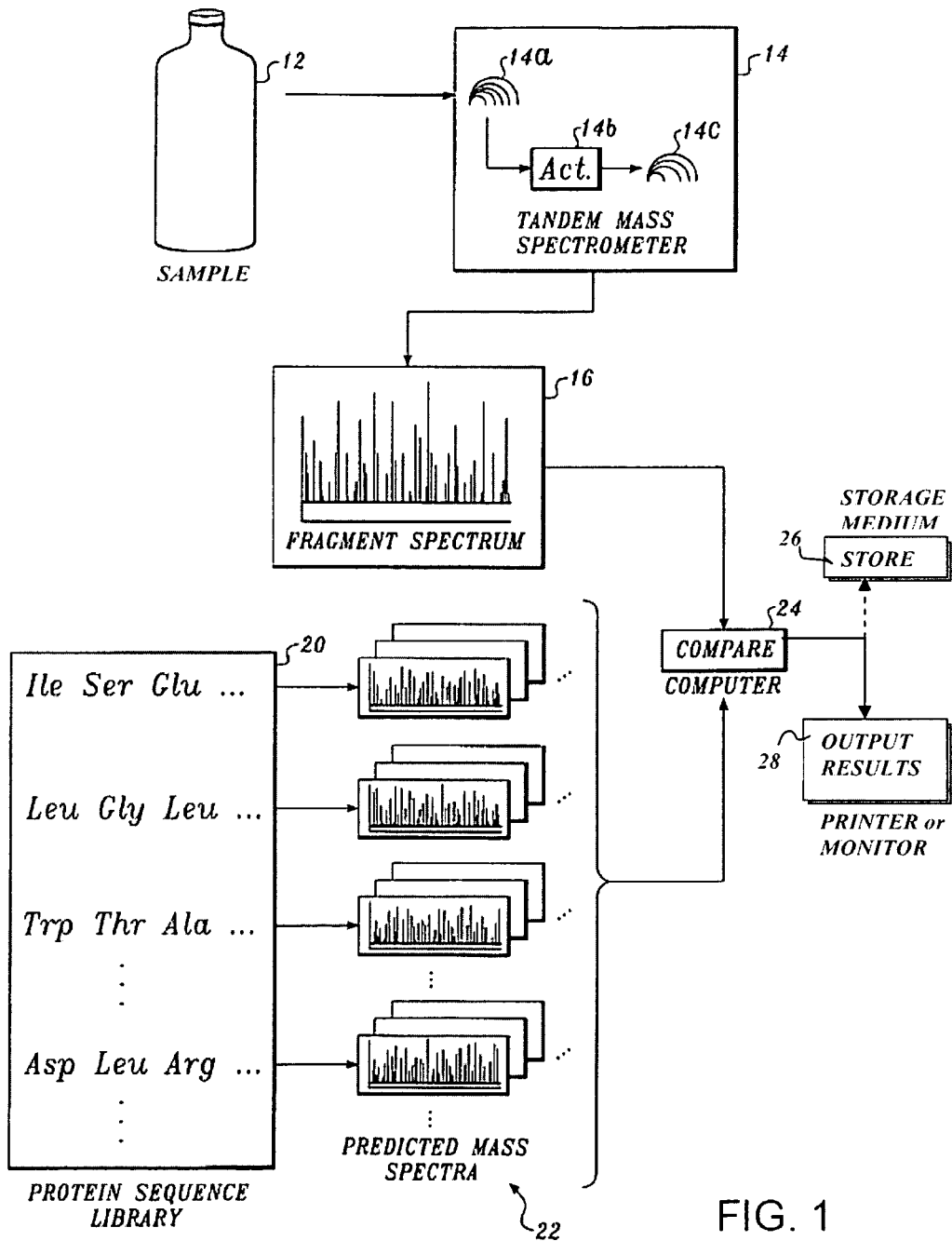
FIG. 1 is a block diagram showing a prior art method for correlating tandem mass spectrometer data with sequences from a protein sequence library

The following definitions are relevant to this description of the invention:

"Spectrum" means a list of numbers (e.g., amino acid masses) with associated intensities.

"Peptide" means any polymer where the sequence of monomers can be expressed as a spectrum (e.g. peptide/protein sequences).

"Sequence" means a string of symbols describing the polymer (e.g. a [possibly modified] protein sequence).

"Modification" means any observable change in the measurable property of a monomer as compared to some reference polymer. Specific examples include post-translational modifications or mutations of amino acid residues. The reference polymer can be any reference, including one that is possibly unknown.

"Parent mass" means the sum of the amino acid masses of a peptide. Parent masses may be computed by aligning the spectra. (See, e.g., Dancik, et al., De novo peptide sequencing via tandem mass spectrometry. *J Comput Biol*, 1999, 6, 327-342. incorporated herein by reference.)

According to the present invention, a spectrum generated by mass spectrometric analysis of a peptide can be represented as an amino-acid graph with vertices for each integer between 0 and M·|S|, where |S| represents the parent mass of the spectrum, and M is a multiplication factor for higher resolution (more than one Da). Vertices corresponding to the peaks in the spectrum are assigned values equal to the rank of the peak. To accommodate low accuracy peaks, all vertices within a threshold distance are also assigned the same value as the vertex with the peak. Vertices whose distance corresponds to an amino acid mass are connected by an edge. Dynamic programming can then be used to compute the number of peptide reconstructions of mass i and score t represented by S(i,t) for all values of i and t.

According to the present invention, a generating function approach is used to accurately compute probabilities p(S) for the individual spectra, thus allowing evaluation of the statistical significance of MS/MS searches using a precise number of identified peptides from a much larger peptide database. This, in turn permits computation of the solution of the Spectrum Matching Problem exactly rather than empirically.

Solving the Spectrum Matching Problem is not unlike computing the generating function in combinatorics. Given a spectrum S and a score X, E(S,X) is the number of peptides (among all possible peptides) that match the spectrum S with score X. To evaluate FPRs one computes E(S, X) for every spectrum S and every score X (more precisely, the sum of probabilities of all peptides contributing to E(S, X)).

According to the present invention, the generating function of tandem mass spectra can be analogized to the classical Ising model of ferromagnetism. The Ising model consists of n magnetic spins such that each spin can be in two states (up and down). This results in $2^n$ possible states each with its own energy defined by the elementary interactions between neighboring spins on the lattice. The partition function represents the technique for analyzing the Ising model and is defined as $$\sum_{\text{all states } \pi} e^{-Energy(\pi)},$$

ignoring the "temperature" parameter of the Ising model.

Interpretation of a spectrum S with a peptide P is similar to choosing a state in the Ising model. Instead of $2^n$ states of magnetic spins, there are $20^n$ possible interpretations of the spectrum S by peptides of length n. Each of these interpretations has its own "energy" given by the score of the match between spectrum S and peptide P (the Energy-score). The goal is to compute the partition (generating) function of the spectrum S and to apply it for analyzing statistics of the MS/MS searches rather than the statistics of the Ising model. While the generating function of tandem mass spectra involves $20^n$ terms, it can still be used for efficient computation.

Figure 2A:
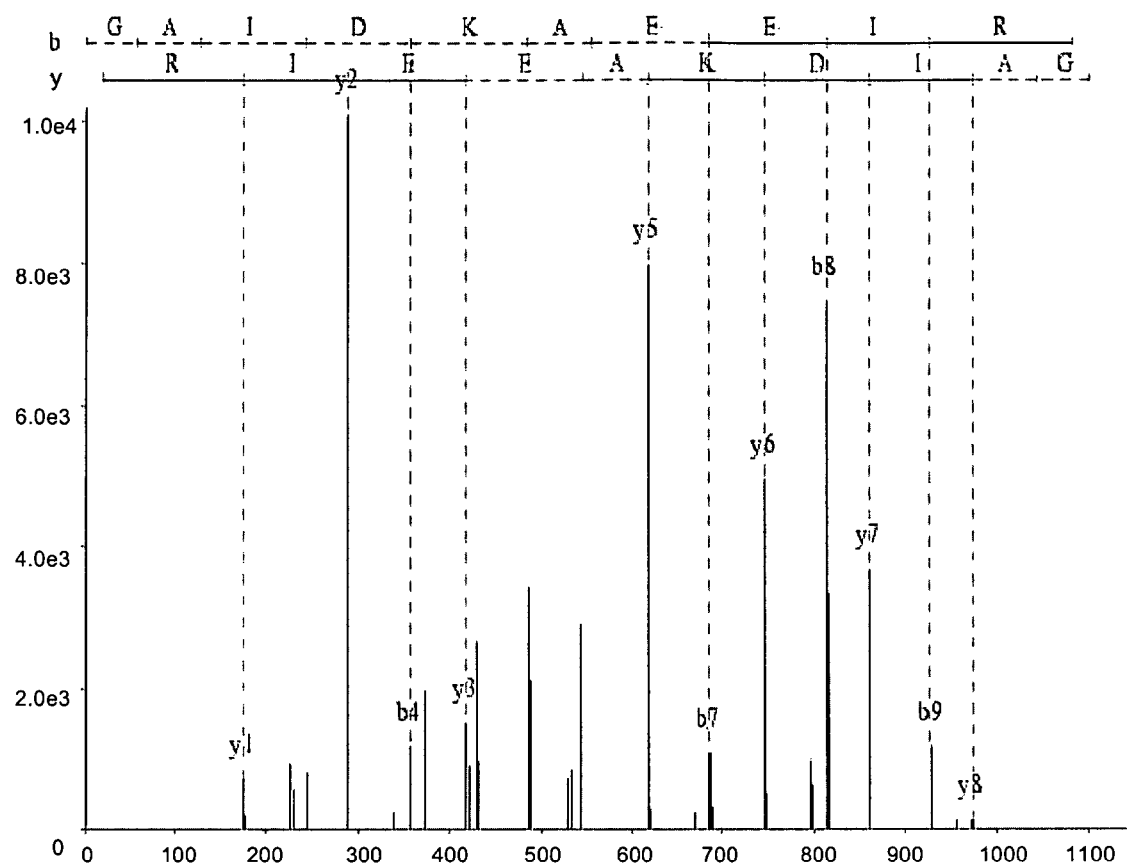

A spectrum matching scheme begins with the general process illustrated in FIG. 1. Referring to FIG. 2a, for a spectrum S of peptide GAIDKAEEIR (SEQ ID NO. 1) (top 43 peaks after removal of low-intensity peaks), the number of peptides (E(S, X)) that explain X b/y peaks in this spectrum are shown in FIG. 2b. FIG. 2b illustrates the notion of the generating function in the simple case when the score X of a match between a spectrum and a peptide is defined as the number of peaks in the spectrum explained as b or y ions. For example, there are 360 peptides with 13 b/y ions explained (E(S, 16)=360), 12940 peptides with 12 b/y ions explained, and so on. The score of the top-scoring database peptide, GAIDKAEEIR fSEQ ID NO. 1), is 11, the optimal score among all possible (candidate) peptides is 13 (such as for the peptide QPMGAEAELR (SEQ ID NO. 2)), thus the "Energy-score" is 2, where the spectral Energy-score represents the difference between the best de novo spectral interpretation and the best database spectral interpretation. (Note that "candidate" peptides are not intended to be restricted to peptides contained in a target database.) While the Energy-score (in contrast to the Δ-score) has been ignored in prior art MS/MS approaches, it can greatly improve the separation between the correct and false identifications. The second top-scoring peptide in the database (DQELLSEIR (SEQ ID NO. 3)) has score 5, giving a Δ-score of 6. For simplicity, a peak that explains both a b-ion and a y-ion in a particular peptide is counted as explaining two b and y peaks. FIG. 2c shows the (uniformly weighted) generating function of the same spectrum. This table shows the number of peptides with score X, the overall probability of peptides with score X and the total probability of all peptides with scores equal to or larger than X (spectral probability). The peptides QIDKAEEIR (SEQ ID NO. 4) and QIDGAAEEIR (SEQ ID NO. 5) represent better spectral interpretations (score 64) than the correct peptide GAIDKAEEIR (SEQ ID NO. 1) that was identified by InsPecT (score 60), resulting in an Energy-score of 4. There are 24 optimal de novo reconstructions that are all derived from QIDKAEEIR fSEQ ID NO. 4) and QIDGAAEEIR fSEQ ID NO. 5) via I/L and Q/K substitutions (16 for QIDKAEEIR (SEQ ID NO. 4) and 8 for QIDGAAEEIR fSEQ ID NO. 5)). The total probability of these 24 peptides is $16 \cdot 20^{-9} + 8 \cdot 20^{-10} = 3.20 \cdot 10^{-11}$. The second best peptide in the database (IRSIESQLR (SEQ ID NO. 6)) has score 27, therefore the Δ-score is 33. Thus, E(S, X) can be used to improve the sensitivity-specificity trade-off of various database search tools.

To provide a simple illustration, a generating function for Boolean spectra ignores intensities, charges, inaccuracies in peak positions, and C-terminal ions. While the Boolean spectra are impractical, they can be useful as a stepping stone for introducing simple scoring/algorithms and later generalizing them to real spectra and more complex algorithms. This will be later expanded to define the generating function for real spectra.

In this example, a Boolean spectrum S has parent mass k as 0-1 vector $s_1 \ldots s_k$, where $s_i=1$ if there is a peak at mass i in the spectrum, and $s_i=0$, otherwise. This representation assumes that the spectra are discretized and all masses are integers, e.g., FIG. 3.

The "match score" between spectra $s_1 \ldots s_k$ and $s'_1 \ldots s'_k$ is defined as $$\sum_{i=1}^{k} s_i \cdot s'_i.$$

Given a peptide $P=p_1 \ldots p_n$, its theoretical spectrum Spectrum (P) is defined as a 0-1 spectrum $s_i \ldots s_k$ with (n−1) 1s, such that $s_i=1$ if i is the mass of the peptide $p_1 \ldots p_i$. The score (denoted as Score(P, S)) between a peptide P and a spectrum S (with the same parent mass) is defined as the match score between spectra Spectrum(P) and S. For convenience, assume that Score(P, S)=−∞ if peptide P and spectrum S have different parent masses. Let SCORE=SCORE(S)=max$_{all\ peptides P}$ Score(P, S) be the maximum value of Score(P, S) among all possible peptides P. SCORE can be estimated using de novo peptide sequencing algorithms. The "energy" of a peptide-spectrum pair is defined as Energy(P, S)=SCORE−Score(P, S). The generating function of the spectrum S is then defined as $$\sum_{all\_peptides\_P} e^{-Energy(P,S)} = \sum_{t} x(t) \cdot e^{-t},$$

where x(t) is the number of peptides with energy t. (This expression represents the exponential generating function of the vector x=(x(0), x(1), . . . ).

Given the probabilities of individual amino acids (e.g., computed empirically from a set of protein sequences), the probability prob(P) of a peptide $P=a_1 \ldots a_m$ is defined as the product of probabilities of its amino acids $$\prod_{i=1}^{m} \text{prob}(a_i).$$

Also consider the weighted generating function:

$$\sum_{all\ peptides\ P} \text{prob}(P) \cdot e^{-Energy(P,S)} = \sum_{t} y(t) \cdot e^{-t},$$

where y(t) is the overall probability of all peptides with energy t.

Given a spectrum S, introduce a variable x(i, t) equal to the number of peptides of mass i that have t peaks in common with spectrum S, i.e., the number of peptides P such that Score(P, $S_i$)=t ($S_i$ stands for "i-prefix" $s_1 \ldots s_i$ of the spectrum S). In this case, S has a peak at position i($s_i$=1), the variable x(i, t) can be computed as follows (|a| denotes the mass of an amino acid a):

$$x(i, t) = \sum_{all\ amino\ acid\ a} x(i - |a|, t - 1)$$

Otherwise ($s_i$=0):

$$x(i, t) = \sum_{all\ amino\ acids\ a} x(i - |a|, t)$$

An equivalent and more compact representation of these recurrences is:

$$x(i, t) = \sum_{all\ amino\ acids\ a} x(i - |a|, t - s_i)$$

Initialize x(0, 0)=1, x(0, t)=0 for t>0, and assume that x(i, t)=0 for negative i. The maximum value SCORE of Score(P, S) among all possible peptides P is simply the maximum value of t with non-zero x(k, t).

Figure 3:
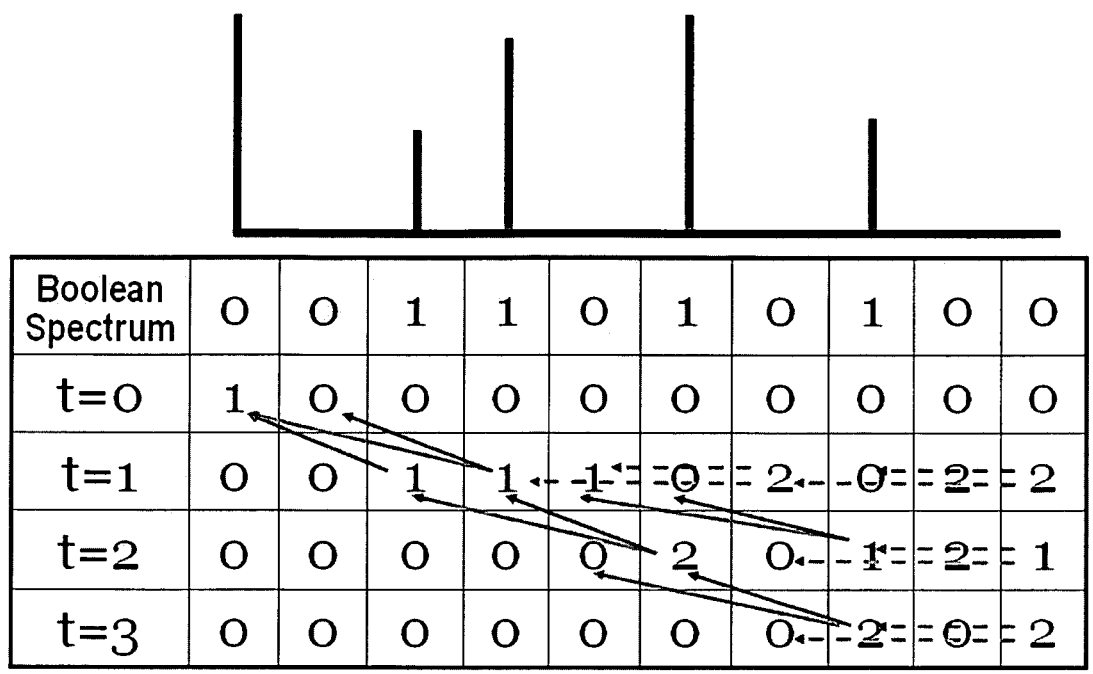
FIG. 3 illustrates the MS-GF dynamic programming algorithm of the present invention as applied to a simplified amino acid model

FIG. 3 illustrates application of the above to two amino acids A and B having masses 2 and 3 Daltons, respectively, and a simplified discretized spectrum (only 4 peaks at 2, 3, 5, and 7 Da). The scoring function used for this illustration is the number of matching prefix ions. The spectrum is converted into its Boolean representation 011010100 with 1's at positions 2, 3, 5, and 7 (the extra zero in the beginning is added to represent the variable x(0, t)). The vertical axis in the dynamic programming table represents scores (t). The value in each cell of the matrix represents the number of peptide reconstructions that explain the initial part of the spectrum till that position with the corresponding score. The first cell in the matrix (0,0) is initialized with 1, and the matrix is filled progressively from left to right and top to bottom. The value of each cell is computed as the sum of the values of previously filled cells which are 2 (black arrows) or 3 (grey arrows) columns before the cell under consideration. If there is a peak at the current position of the spectrum, the sum is taken over the cells in the previous row, otherwise in the same row. In this example, the maximum achievable score (t) is 3, which can be obtained by two peptide reconstructions. The sequences of these reconstructions can be obtained by backtracking, as indicated by the arrows, and are found to be ABAA and BAAA. As shown, there are two reconstructions with score 1 and one reconstruction with a score of 2.

The recurrence for computing the weighted generating function is similar. In this case, the variable y(i, t) equals to the overall probability of peptides of mass i that have t peaks in common with spectrum S. The variable y(i, t) is initialized in the same way as x(i, t), with x(0, 0) initialized as 1, since the "empty" peptide is the only peptide with mass 0 that has 0 peaks in common with the spectrum S, and y(0, 0) initialized as 1, since the probability of the empty peptide is defined as 1.

$$y(i, t) = \sum_{\text{all amino acids } a} x(i - |a|, t - s_i) \cdot \text{prob}(a)$$

The above algorithm for computing the generating function has complexity $O(|S| \cdot |\text{SCORE}| \cdot \text{Mult} \cdot \text{PeptideLength} \cdot A)$, where A=20 is the number of amino acids, PeptideLength is the maximum length of a peptide with the mass equal to $|S|$, and Mult is the multiplication coefficient that was applied to all masses in the spectrum to satisfy the assumption that they are integers (typically, Mult=10 for ion-traps). In practice, it requires 0.1-0.2 seconds to compute the generating function on a desktop machine with 2.16 GHz INTEL® processor.

To compute the generating function for real spectra, the inventive MS-GF ("mass spectrometry-generating function) transforms tandem mass spectra into its integer-valued scored version $s_1 \ldots s_k$ (rather than Boolean spectra) using the probabilistic model similar to that described by Dancik, V. et al., "De novo peptide sequencing via tandem mass spectrometry", *J. Comput Biol* 1999, 6, 327-342, which is incorporated herein by reference. This model is described briefly below.

The goal of scoring is to quantify how well a candidate peptide "explains" a spectrum and to choose the peptide that explains the spectrum the best. If p(P,S) is the probability that a peptide P produces spectrum S, then the goal is to find a peptide P maximizing p(P,S) for a given spectrum S. The following describes a probabilistic model, evaluates p(P,S), and derives a rigorous scoring schema for paths in the spectrum graph (versus largely heuristic previous approaches). The longest path in the weighted spectrum graph corresponds to the peptide P that "explains" spectrum S the best.

In a probabilistic approach, tandem mass spectrometry is characterized by a set of ion types $\Delta = \{\delta_1, \ldots, \delta_k\}$ and their probabilities $\{p(\delta_1), \ldots, p(\delta_k)\}$ such that $\delta_i$-ions of a partial peptide are produced independently with probabilities $p(\delta_i)$. A mass spectrometer also produces a "random noise" that in any position may generate a peak with probability $q_R$. Therefore, a peak at a position corresponding to a $\delta_i$-ion is generated with probability $q_i = p(\delta_i) + [1 - p(\delta_i)]q_R$ that can be estimated from the observed empirical distributions. A partial peptide may theoretically have up to k corresponding peaks in the spectra. It has all k peaks with probability $$\prod_{i=1}^{k} q_i$$

and it has no peaks with probability $$\prod_{i=1}^{k} (1 - q_i).$$

The probabilistic model defines the probability p(P,S) that a peptide P produces spectrum S. Computation of p(P,S) is described below along with the method to derive scoring that leads to finding a peptide that maximizes p(P,S) for a given spectrum P.

Suppose that a candidate partial peptide $P_i$ produces ions $\delta_i, \ldots, \delta_l$ ("present" ions) and does not produce the ions $\delta_{l+1}, \ldots, \delta_k$ ("missing" ions) in the spectrum S. These l "present" ions will result in a vertex in the spectrum graph corresponding to $P_i$. The existing database search algorithms use "a premium for explained ions" and/or "penalty for unexplained ions" approach, suggesting that the score for this vertex should be proportional to $q_1 \ldots q_l$ or maybe $q_1/q_R \ldots q_l/q_R$ to normalize the probabilities against chemical and electronic noise. (The ratios $q_i/q_R$ can be taken from the offset frequency function.) Significant improvement results from penalizing for the non-presence of ions in the experimental spectrum, which is possible from fragmentation of a candidate sequence. Thus, the (probability) score of the vertex is determined by assigning premium for present ions, and a penalty for missing ions.

The probabilistic transformation of tandem mass spectra into its integer-valued scored version takes into account peptide length, peak intensities, neutral losses, dependencies between ion types, noise, etc. Most de novo and database search algorithms use such a representation, either explicitly or implicitly, by assigning intensity-dependent scores to peaks, further adjusting for imprecisions in mass-measurements, and applying the dot-product for scoring spectra against peptides. However, these scores are typically attached to the positions of peaks in the spectrum $s_1 \ldots s_k$ and will not enable a computation of the generating function in the low-accuracy setting with accuracy threshold $\delta$. However, as long as the spectrum $s_1 \ldots s_k$ as $s'_1 \ldots s'_k$ is redefined with $S'_i = \max_{j=i-\delta}^{j=i+\delta} s_j$, the generating function (in case of imprecise mass measurements) can be easily computed as described below.

The score Score(P, S) between a peptide P and a spectrum S (with the same parent mass) is defined as the dot-product between the theoretical spectrum Spectrum(P) and S (now S is defined as an arbitrary integer-valued vector and Spectrum (P) is defined to allow for both N-terminal and C-terminal ions). Let SCORE be the maximum value of Score(P, S) and Energy(P, S)=SCORE-Score(P, S). Given a spectrum S, x(i, t) is defined as the number of peptides of mass i with score t, i.e., the number of peptides P such that Score(P, $S_i$)=t. The variable x(i, t) can be computed as in the case of Boolean spectra.

It should be noted that MS-GF can handle scored spectra generated by any MS/MS tool with additive scoring functions. The scoring function chosen herein can be viewed as a variation of SHERENGA and PepNovo with improved analysis of peak intensities and doubly charged ions. Some MS/MS analysis tools (e.g., SEQUEST or tools using sequence-specific peak intensities) have non-additive scoring components and thus cannot be modeled by this generating function framework. Nonetheless, MS-GF still can be used to re-score their results.

Let A be a peptide identification algorithm that accepts a peptide P as an interpretation of a spectrum S as long as the peptide-spectrum score Score(P, S) is larger or equal to the threshold T. Given the allowed (integer) parent mass error $\epsilon$, the weighted generating function allows computation of the overall probability of peptides with scores equal to or larger than T (spectral probability) as $$\text{prob}_T(S) = \sum_{i=ParentMass-\epsilon}^{i=ParentMass+\epsilon} \sum_{t \geq T} y(i, t)$$

For example, the spectral probability $\text{Prob}_{60}(S)=2.76 \cdot 10^{-10}$ represents the total probability of all 306 peptides with scores larger or equal to the score of the correct peptide in FIG. 2c. The probability that the algorithm A identifies the spectrum S in a random database of size n is computed as $1-(1-\text{Prob}_T(S))^n$. Since the parameter T is usually chosen in such a way that $\text{Prob}_T(S)$ is much smaller than 1/n, one can assume that $1-(1-\text{Prob}_T(S))^n \approx \text{Prob}_T(S) \cdot n$. If a user attempts to identify peptides with a fixed FPR in a database of size n (e.g., FPR=0.01 is commonly used in MS/MS searches), then the parameter T is chosen in such a way that $$\text{prob}_T(S) = \frac{FRP}{n}.$$

The corresponding value of T can be derived from the generating function (see, e.g., the third column in FIG. 2c).

Example 1

Shewanella Dataset

The Shewanella oneidensis MR-1 dataset used in this example (14.5 million spectra) and peptide identifications based on this dataset are described by Gupta, N., et al., "Whole proteome analysis of post-translational modifications: applications of mass-spectrometry for proteogenomic annotation", *Genome Res.* 2007, 17, 1362-1377. 28,377 unmodified peptides were identified in this dataset by InsPecT with an error rate of 5% (1% spectrum-level error rate) as measured using a decoy database. (Tanner, S.; et al.,. "InsPecT: identification of posttranslationally modified peptides from tandem mass spectra", *Anal Chem.*, 2005, 77, 4626-4639.

Due to its large size, searching the entire Shewanella dataset with tools like SEQUEST is prohibitively time-consuming. To make it easier to benchmark the inventive approach against other tools and to summarize the results, two smaller datasets (geared to peptides of length 10) are used in this study. These datasets are identified as:

Shewanella-1784: From 28,377 peptides identified in Shewanella oneidensis MR-1, all doubly-charged tryptic peptides of length 10 were selected. This resulted in 1745 and 39 peptides identified in the target and decoy databases, respectively (2.2% error rate). For each of these 1745+39=1784 peptides, one spectrum (chosen randomly if the peptide is identified from multiple spectra) was retained to construct the final dataset of 1784 spectra.

Shewanella-50000: From all 14.5 million Shewanella spectra, 50,000 doubly-charged spectra with parent masses ranging from 1100 to 1200 Da were selected. (These spectra typically correspond to peptides of length$\approx$10 aa.) Each spectrum in this dataset was searched against all Shewanella proteins (1.47 million of amino acids) and against the randomized decoy database (of same size) with SEQUEST (TurboSEQUEST v.27, rev. 12), InsPecT (20060907), and X!Tandem (2007.01.01.2), as well as analyzed with MS-GF and PeptideProphet (v3.0).

A comparison showed that the error rates reported by existing database search tools do not provide accurate estimates of the statistical significance of individual peptide identifications (they are often off by an order of magnitude) while the error rates evaluated by MS-GF are very accurate.

To evaluate whether MS-GF accurately estimates the number of hits in the decoy database (thus eliminating the need for the decoy database search) the following experiment was conducted. For each spectrum in the Shewanella-50000 dataset, the top-scoring peptides whose total probability sums up to the parameter SpectralProbability were generated. A spectrum is considered identified in a database if any of the generated reconstructions is present in the database. The value of SpectralProbability was varied to compute the number of spectra that were identified in the Shewanella database and the decoy database of the same size. Table 1 shows the distribution of these numbers, compares them against SpectralProbability$\cdot$n$\cdot$50000 (the expected number of matches in the database of size n) and shows that the number of matches in the decoy database is very close to the expected number of matches computed by MS-GF.

TABLE 1

| Spectral-Probability | # Correct IDs (in target DB) | # False IDs (in decoy DB) | # False IDs (predicted by MS-GF) |
| --- | --- | --- | --- |
| 2e−9 | 8314 | 161 | 146 |
| 1e−9 | 7721 | 76 | 75 |
| 8e−10 | 7525 | 60 | 59 |
| 6e−10 | 7272 | 44 | 44 |
| 5e−10 | 7115 | 34 | 37 |
| 4e−10 | 6937 | 28 | 29 |
| 2e−10 | 6333 | 15 | 15 |
| 1e−10 | 5755 | 6 | 7 |
| 1e−11 | 3820 | 0 | 0.7 |

Table 1 lists the number of spectra in Shewanella-50000 dataset that are identified in the Shewanella database (Column 2) and the decoy database (Column 3) by top peptide reconstructions with probability SpectralProbability. Column 4 provides the expected number of spectra that will match the decoy database given SpectralProbability, as computed by MS-GF without actually doing the search.

Figure 4A:
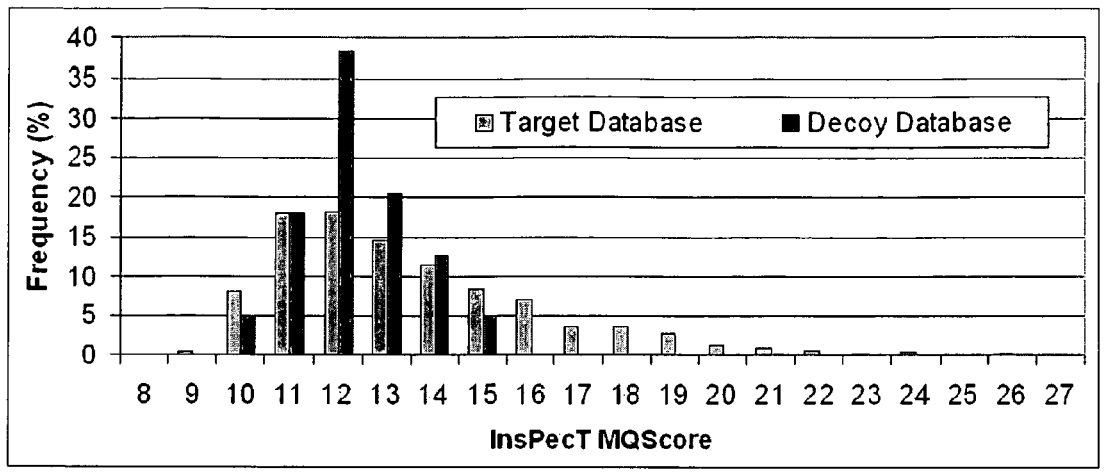
FIGS. 4a-4d are plots showing separation between correct and incorrect identifications as determined us InsPecT MQScore (FIG. 4a), X!Tandem E-Value (FIG. 4b), Energy (P,S) (FIG. 4c), and Spectral Probability of the pair (P,S) (FIG. 4d) for the peptides identified in *Shewanella*-1784 dataset against *Shewanella* and decoy databases.
Figure 4B:
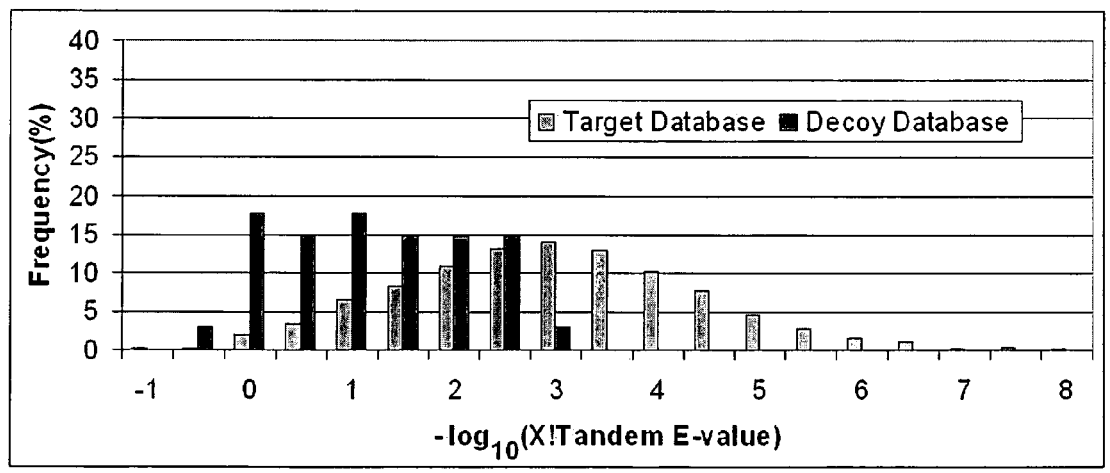

FIGS. 4a and 4b show the distributions of InsPecT and X!Tandem scores for the peptides identified in Shewanella-1784 dataset against the target and decoy database. X-axes show the database search scores, and Y-axes show the fraction of identifications with that score. Advanced peptide identification tools are expected to have similar score distributions in target and decoy databases (otherwise, the difference between the distributions can be used to better separate the correct and false identifications). For InsPecT, the distributions in the target and decoy databases are similar, with a Kolmogorov-Smirnov (KS) distance of 0.28, indicating that InsPecT scoring cannot further differentiate between the correct and the false identifications. In the case of X!Tandem E-value, the KS score is 0.58, indicating that there is some separation between the distributions in target and decoy database, however the distributions still have a large overlap and it is unclear what additional features can separate the correct and false identifications.

Figure 4C:
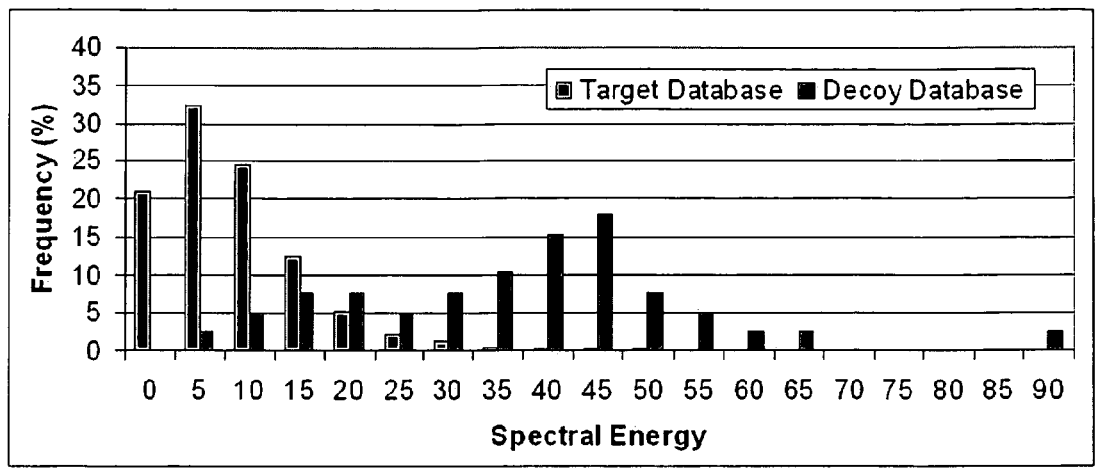
Figure 5:
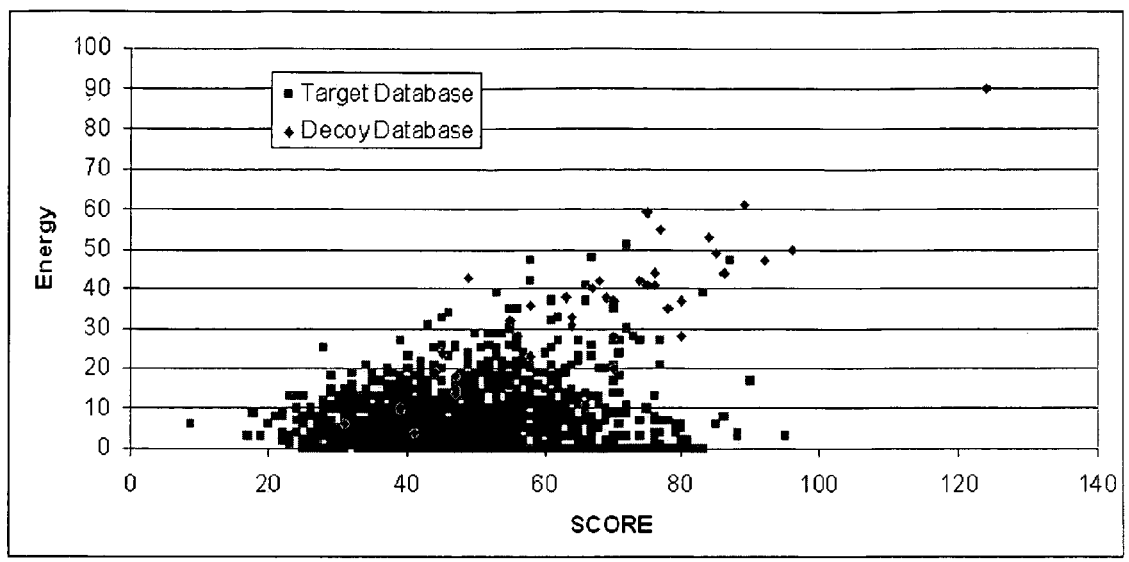
FIG. 5 is a scatter plot showing the joint distribution of SCORE and Energy for the peptides identified in the *Shewanella* database and the decoy database.

FIG. 4c shows the distribution of Energy(P, S) for identifications from *Shewanella*-1784 dataset and demonstrates that spectral energy provides an excellent separation (KS distance is 0.77) between the correct and false identifications. In particular, Energy=0 for a significant portion of correct identifications (in these cases, the identified peptide also represents an optimal de novo reconstruction). The false identifications, on the other hand, have no identifications with Energy=0. Moreover, the separation in FIG. 4c indicates that the Energy is complementary to many other parameters used for scoring spectra (recall that InsPecT scoring combines seven parameters but still does not attain the separation power of Energy). FIG. 5 further shows the joint distribution of SCORE and Energy and provides an intuitive explanation of why the generating function approach improves the sensitivity/specificity ratio of existing MS/MS search tools. Note that the target and decoy identifications are well separated in 2-D, with low SCORE and Energy for the target database and high SCORE and Energy for the decoy database. The black diamonds (decoy database) are laid over the gray squares (*Shewanella* database), so that all decoy database identifications are visible.

Figure 4D:
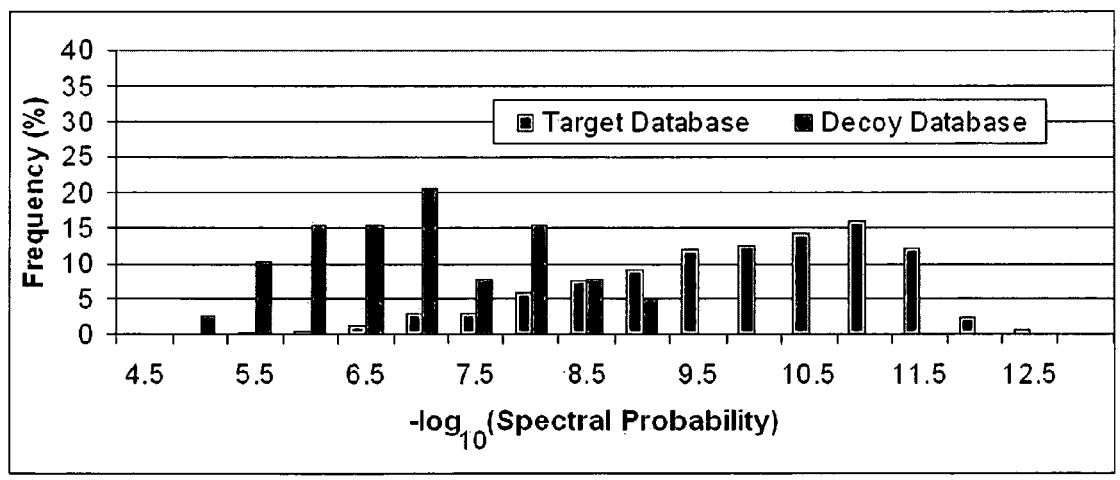

Let Score(P, S) be the match score of a peptide P and a spectrum S. The spectral probability $Prob_{Score(P, S)}(S)$ of the peptide-spectrum pair (P, S) is denoted as the sum of probabilities of all peptides with match scores larger than or equal to Score(P, S) (when compared to S). FIG. 4d shows the distribution of the $\log_{10}$(SpectralProbability (as computed by MS-GF) for correct and false peptide identifications, with a KS of 0.78. Spectral Probability of the pair (P, S) is defined as the sum of probabilities of all peptides whose score is larger or equal to the score Score(P, S) of the match between peptide P and spectrum S. This parameter also provides excellent separation between the correct and false identifications, with false identifications typically having much larger spectral probabilities $Prob_{Score(P, S)}(S)$. This is in agreement with FIG. 4c, further confirming that most identifications on the decoy database, in spite of their high scores, actually represent poor (sub-optimal) de novo solutions, and could be distinguished from correct solutions using MS-GF.

Generating functions can be used to re-score the identifications obtained by various database search tools and to improve the sensitivity-specificity trade-off. This result can be illustrated using *Shewanella*-50000 dataset searched against the target *Shewanella* database and the decoy database using X!Tandem. The existing database search tools use two types of scores that are referred to as "raw" and "combined" scores. Raw scores (used for scanning databases) are defined by a spectrum and a peptide alone, without any reference to the scores of other peptides encountered in the database search. The database-dependent combined scores integrate raw scores with other information such as Δ-score of the second best peptide match (as in SEQUEST), or the distribution of scores of all peptides in the database (like in X!Tandem). The generating function (and the spectral probability) represents the raw score since it does not use any additional information about other peptides in the database. Below, it can be seen that the spectral probability improves on previously proposed raw scores and even outperforms the combined scores of the existing database search tools.

For each spectrum in the *Shewanella*-50000 dataset, three different scores are used for analyzing the peptide identifications and constructing receiver operating characteristic (ROC) curves: (i) X!Tandem raw score used for scanning the database (indicated in FIGS. 6a and 6b by triangles), (ii) X!Tandem combined score (E-value) that integrates the raw score with the distribution of the scores for all peptides in the database (indicated by squares), and (iii) spectral probability as reported by MS-GF for the X!Tandem identification (indicated by circles). For each score, a varying cutoff is used, and the number of spectra that have an identification with scores above the cutoff in the *Shewanella* database and the corresponding error rate (ratio of the number of identifications on a decoy database of the same size and the number of identifications in the target database) are plotted in FIG. 6a.

MS-GF results in a significantly higher number of identifications in the *Shewanella* database for a given error rate (number of identifications on the decoy database) when compared to the raw X!Tandem scores. Similarly, it significantly improves on SEQUEST and PeptideProphet. FIG. 6b shows similar curves for the number of unique peptides instead of the number of spectra. For 5% error rate, X!Tandem raw/combined score identifies 1449/1613 peptides, while MS-GF identifies 1837 peptides. The advantage of MS-GF is particularly pronounced for extremely accurate identifications. For example, for 0.3% error rate (very few false identifications) MS-GF identified 1326 peptides while X!Tandem identified 943/1050 peptides with raw/combined scores. Such extremely accurate identifications are important for a notoriously difficult problem of identifying proteins based on a single peptide hit (one-hit-wonders). Indeed a single peptide hit with the error rate 0.3% may be more reliable than two peptide hits with the error rate 3% each. The fact that MS-GF has better sensitivity-specificity than even the combined X!Tandem score is surprising since MS-GF has no access to the valuable information about other peptides in the database that is incorporated into the combined X!Tandem score. Hence, the spectral probability represents a valuable addition to the various "raw" scores proposed for MS/MS searches to date.

Figure 6A:
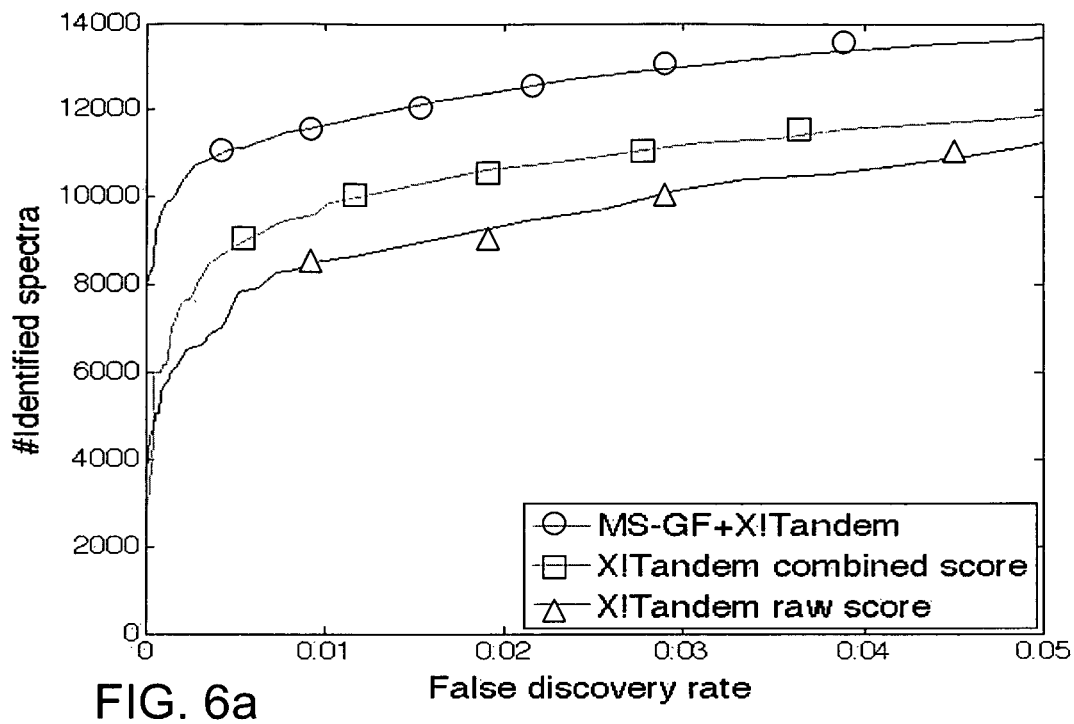
FIGS. 6a and 6b are plots of receiver operating characteristic curves the number of spectra identified (FIG. 6a) and number of unique peptides identified (FIG. 6b) in a comparison of MS-GF with X!Tandem.
Figure 6B:
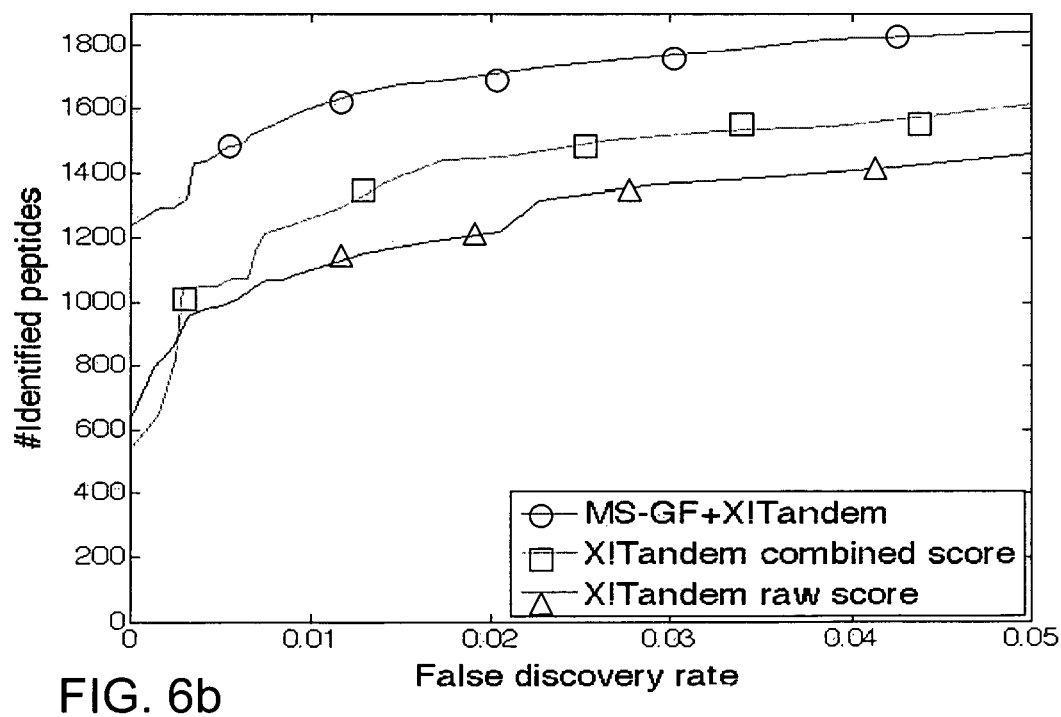

It should be noted that the MS-GF+X!Tandem curves in FIGS. 6a and 6b were was constructed using the information about matches in the decoy database. The superior performance of MS-GF+X!Tandem over X!Tandem raises a question whether a database search based on MS-GF (i.e., using SpectralProbability as a score) would be better off on its own (without using matches identified by X!Tandem).

Figure 7A:
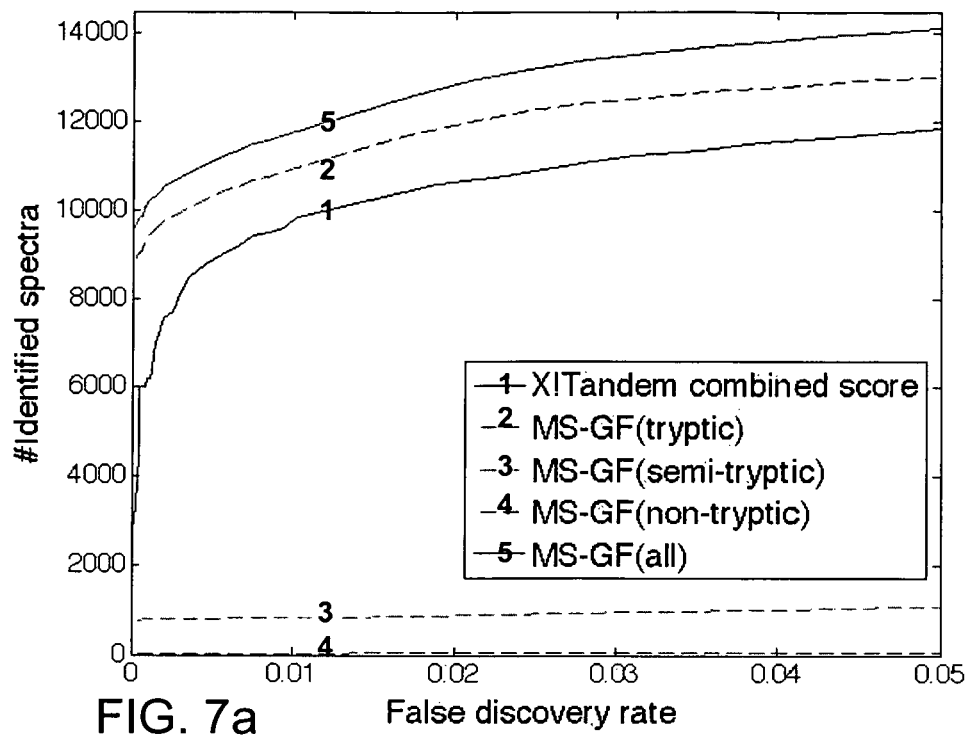
FIG. 7a is a plot of ROC showing the number of spectra identified in the *Shewanella* database and the corresponding error divided into three groups, depending on the peptide endpoints.
Figure 7B:
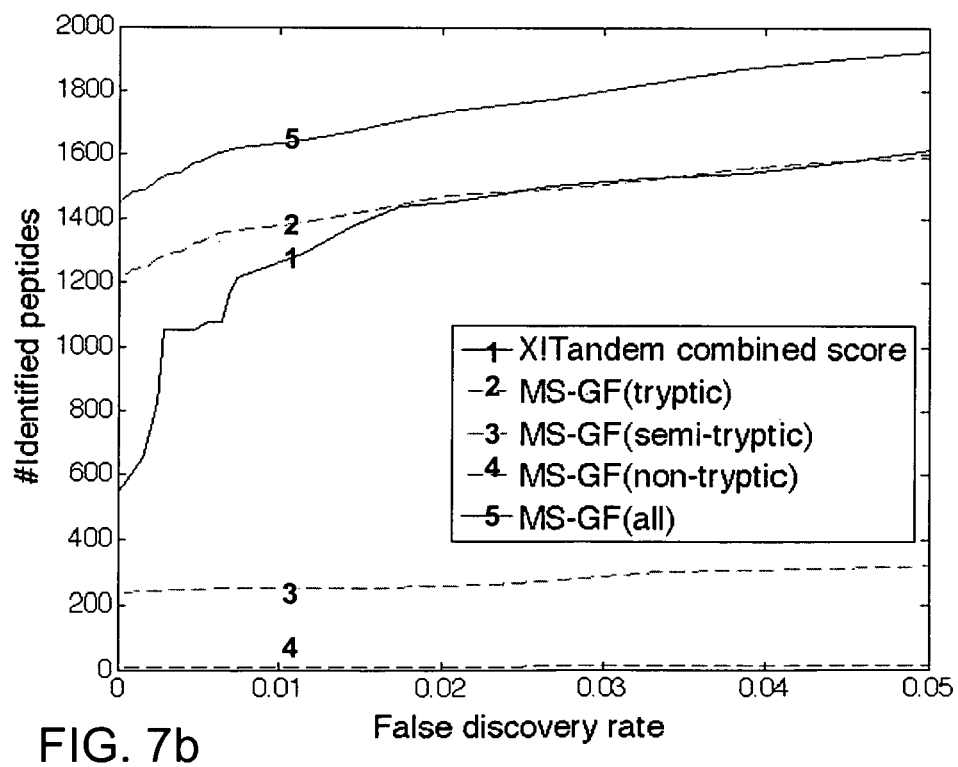
FIG. 7b is the same as FIG. 7a for the number of unique peptides identified.
Figure 8:
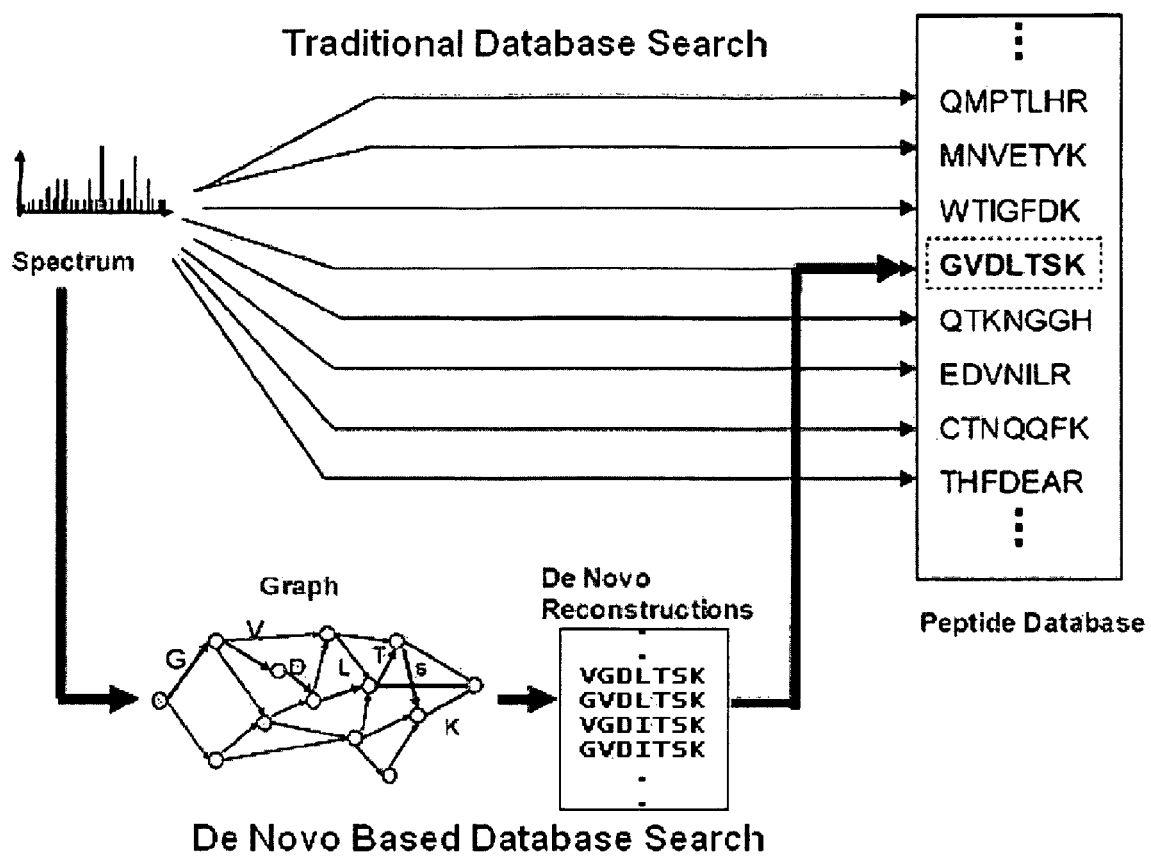
FIG. 8 illustrates two approaches to peptide identification: a traditional approach based on comparing spectra to the database and a hybrid approach according to the invention.
Figure 10A:
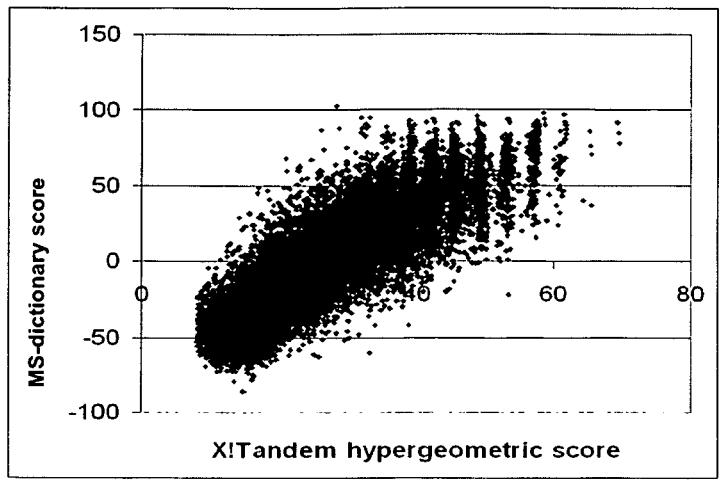
FIGS. 10a-c show correlations of the results of the method according to the present invention (PF-Novo) and two prior art database search tools.
Figure 10B:
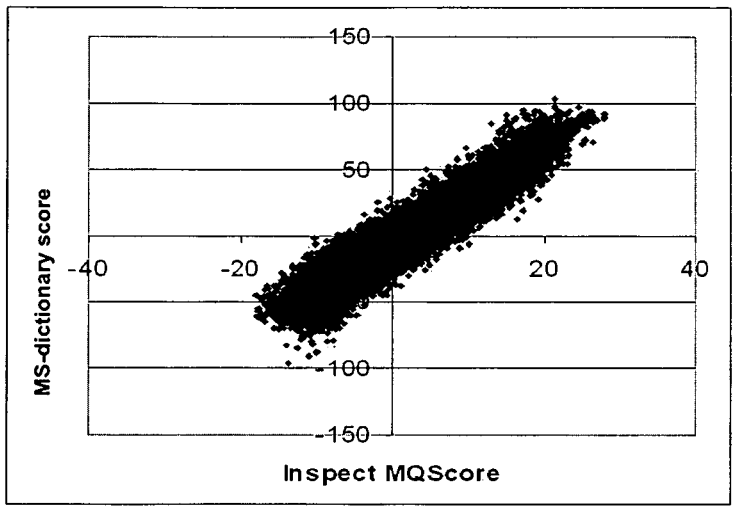
Figure 10C:
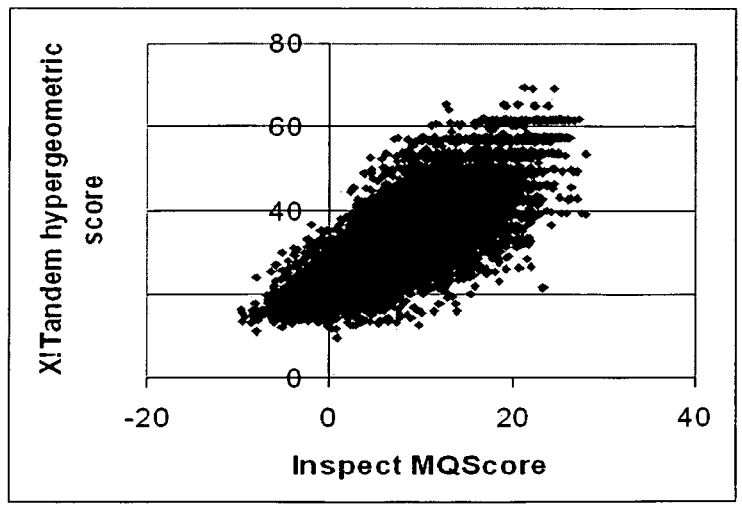

FIGS. 7a and 7b illustrate that MS-GF alone (without using X!Tandem identifications) performs better than X!Tandem. For each spectrum in the *Shewanella*-50000 dataset, the top-scoring peptides whose probabilities sum up to the parameter SpectralProbability were generated. The spectral identifications in the *Shewanella* and decoy databases were divided into three groups, depending on whether the peptide endpoints were consistent with trypsin cleavage specificity: tryptic (both endpoints consistent), semi-tryptic (only one endpoint consistent) and non-tryptic (both endpoint inconsistent). By partitioning into these three groups, it is possible to demonstrate that MS-GF generates more tryptic peptides than the total number of peptides generated by X!Tandem. A spectrum is considered identified in a database if any of the generated reconstructions is present in the database. The value of Spectra/Probability was varied and the number of spectra that were identified in the *Shewanella* database and the decoy database of the same size was computed. This essentially mimics the database search with the spectral probability as the scoring function computed by MS-GF. FIGS. 7a and 7b provide a comparison between the number of identifications made by MS-GF and X!Tandem. Despite the fact that X!Tandem combined score utilizes information that MS-GF does not have access to, MS-GF outperforms X!Tandem. In addition, MS-GF, accurately estimates the number of hits in decoy database thus eliminating the need for the decoy database search altogether. This observation illustrates that computing scores over all possible peptides is better than observing scores over the relatively small decoy database.

Interpreting the "one-hit-wonders" is a difficult problem that often amounts to manual validations. The subjective nature of such inferences have resulted in the Proteomics Publication Guidelines to virtually discard single-hit protein identifications. In a large scale study, this inevitably results in the loss of large amounts of valuable information. For example, there are 402 proteins with single peptide hits in *Shewanella oneidensis* MR-1 as opposed to 1992 proteins with multiple hits (over 20% of the expressed proteome). (For typical bacterial MS/MS projects, the percentage of one-hit-wonders is closer to 30%.) While it was estimated that nearly 75% of these "one-hit-wonders" are correct identifications, no means were available to objectively separate them from the false identifications. Below it is shown how MS-GF (that provides a superior separation between correct and incorrect peptide identifications for low error rates) can be used for reliable identification of the single-hit proteins.

SpectralProbability was calculated for peptides identified in the decoy database in the Public *Shewanella* Datasets, Release No. PNNL-SA-52859 available from Pacific Northwest National Laboratory (on the World Wide Web at biodemo.pnl.gov) (1417 peptides were identified in the decoy database as compared to 28,377 peptides identified in the *Shewanella* database.) From 1417 peptides, the Charge-2 and unmodified peptides were selected for this analysis, giving 1065 peptides. The lowest value of Spectra/Probability among all these decoy identifications was $1.55 \times 10^{-8}$.

Similarly, SpectralProbability was computed for the peptides from the single-hit proteins and the spectral probability for 345 of them was lower than $1.55 \times 10^{-8}$. These 345 peptides represent better identifications than every identification in the decoy database, and the corresponding proteins must be considered reliably identified with virtually zero empirical error rate. It is worth noting that many single-hit-wonders with SpectralProbability below $1.55 \times 10^{-8}$ are actually more statistically significant than some proteins with multiple peptide hits but larger SpectralProbability values for combining peptide significance scores into protein significance scores).

The prior art approaches compute the error rates based on approximate fitting of the empirical distributions to a standard distribution that may not carefully reflect the specifics of an individual spectrum. Moreover, they assume the same null hypothesis for all spectra in the sample, the assumption that may not be adequate for mass spectrometry searches. In contrast, the inventive MS-GF approach described herein does not assume any "null hypothesis" or "noise model" for spectra generation. Further, it does not assume any particular approximation for the tail of the score distribution. Instead, it rigorously solves the Spectrum Matching Problem, the same problem the existing approaches attempt to solve via decoy databases and various approximations.

MS-GF allows accurate estimation of the statistical significance of individual spectral interpretations. As described above, MS-GF can be used either to complement the decoy searches or on its own. The former case illustrates the synergy between the decoy database and the generating function approaches in cases when the generating function framework can only be applied to the results of the decoy database searches. This is particularly relevant for estimating the error rates of protein identifications, re-scoring of complex non-additive scoring functions, or projects that can tolerate higher error rates. The generating function approach can be further used to generate a list of all peptides whose score exceeds a threshold and match these peptides in the protein database, thus enabling a hybrid approach to peptide identification.

While the generating function described herein evaluates the statistical significance over the set of all unmodified peptides, it can be extended to analyze modified peptides in both restricted and blind modes. The former case amounts to adding "modification edges" of fixed length while the latter case amounts to adding modification edges of arbitrary length to the amino acid graph. The dynamic programming in the resulting graph should take into account the maximum allowed number of modifications per peptide.

In another aspect of the invention, the generating function introduced above is used as the basis for a de novo search tool referred to herein as a "spectral dictionary", or "MS-dictionary" (for (mass spectral dictionary). As previously described, the generating function approach analyzes the number of peptide reconstructions with optimal and suboptimal scores and helps to determine the significance of those reconstructions. In the context of de novo search, the same approach is useful for determining the number of reconstructions that should be reported for any spectra. A new scoring is used to accurately reflect the statistics of fragment ions rather than chasing an elusive goal of assigning the maximum score to the correct peptide.

The inventive process begins with an abstract model that seemingly has nothing to do with de novo peptide sequencing but rather describes a very general probabilistic process that transforms one Boolean string into another. This process not only generalizes the probabilistic model for de novo peptide sequencing but also allows one to compute the generating function of tandem mass spectra.

Let $s = s_1 \ldots s_n$ be a Boolean string called a "spectrum" and $\pi = \pi_1 \ldots \pi_n$ be a Boolean string called a "peptide". The probability of peptide $\pi$ generating spectrum s is defined as $$\text{Prob}(s \mid \pi) = \prod_{i=1}^{n} \text{Prob}(s_i \mid \pi_i),$$

where Prob(x|y) is a 2×2 matrix:

| x | y | |
|---|---|---|
|   | 1 | 0 |
| 1 | $\rho$ | $\theta$ |
| 0 | $1 - \rho$ | $1 - \theta$ |

Given a spectrum s and a set of strings $\Pi$, the goal is to solve the optimization problem $\max_{\pi \in \Pi} \text{Prob}(s \mid \pi)$. Focusing on the sets $\Pi$ that are relevant in the context of tandem mass spectrometry, let V={1, ..., n} and G(V,E) be a topological ordering of a DAG (Directed Acyclic Graph) such that i<j for every directed edge (i,j) in E. Every path from 1 to n in G corresponds to a G-peptide $\pi=\pi_1 \ldots \pi_n$ such that $\pi_i=1$ iff vertex i belongs to the path. See, e.g., FIG. 15, which is an amino acid graph G for all peptides with a parent mass 7 and only two possible amino acids A and B with masses 2 and 3, respectively. The highlighted path corresponds to the G-peptide 0101001 corresponding to AAB (masses of consecutive amino acid masses are 2, 2, 3). Two other G-peptides with parent mass 7 are 0100101 (ABA) and 0010101 (BAA). In the context of the above equation for the probability of a spectrum s being generated by a peptide $\pi$, $\pi=10101001$ and s=0001101 (P(s=0001101, $\pi=10101001)=\theta\cdot(1-\theta)^3\cdot\rho^2\cdot(1-\rho)$).

The Peptide Sequencing (PS) Problem is: given a spectrum s and a DAG G, find a G-peptide $\pi$ that maximizes Prob(s|$\pi$) over all G-peptides.

No restrictions are imposed on the graph G(V,E), however, in de novo peptide sequencing by tandem mass spectrometry (MS/MS) it is usually assumed that (i,j) ∈ E iff (j−i) equals the integer mass of an amino acid. Such graphs are referred to as "amino acid graphs" (compare to spectrum graphs, which are generally known in the art). As a first approximation, a MS/MS spectrum with a parent mass n can be represented as a string of ones (peak present) and zeros (no peak present), with a 0/1 for every consecutive 1 Da interval. Similarly, sequences of amino acid masses (peptides) can also be represented as strings of zeros and ones. An amino acid of mass α can be represented as a string of (α−1) zeros followed by a single one ("1"). Then, a peptide is simply a concatenation of Boolean strings corresponding to its amino acids. In this context, $\theta\approx0.05$ (probability of observing a noise peak) and $\rho\approx0.7$ (probability of observing a b-ion) represent typical values of θ and ρ for ion-trap MS/MS spectra (see above matrix). This somewhat simplistic Boolean string model can be modified for any mass resolution, peptide fragmentation rules and peak intensities. The modifications of this model incorporating these details are described below.

The model above does not capture the fact that MS/MS spectra represent both prefix ions (b-ions series) and suffix ions (y-ions series). To reflect this, peptides are represented as strings in a 3-letter alphabet: 1 (theoretical b-cut), −1 (theoretical y-cut), and 0 (no cut). Given a peptide $\pi=\pi_1\ldots\pi_n$, its reverse is defined as the peptide $\pi^*=-\pi_n \ldots -\pi_1$, i.e., $\pi^*=-\pi_{n-i+1}$. The probability of peptide $\pi$ generating spectrum s is now defined as $$Prob(s|\pi) = \prod_{i=1}^{n} Prob(s_i|\pi_i) \cdot Prob(s_i|\pi_i^*), \text{ where } Prob(x|y) \text{ is a}$$

2·3 matrix.

where Prob(x|y) is a 2·3 matrix.

While the simple model described above led to an accurate peptide sequencing algorithm, it does not capture the intensities of fragment ion in MS/MS spectra. The experimental spectra represent real valued vectors $s_1 \ldots s_n$ rather than Boolean vectors ($s_i$ is the peak intensity at mass i). One can argue that the same model based on probabilities P(x,y) where x is a (real valued) peak intensity and y∈{−1,0,+1} would take into account the intensities of mass spectra. However, this model faces difficulties since: (i) intensities may vary between spectra of the same peptide taken at different times/experiments; and (ii) the value of intensity seems to be less important than the distribution of intensities over different peaks. As a result, most current peptide sequencing algorithms use heuristic approaches to modeling intensities and do not try to derive a model of spectra generation that accounts for intensities. In contrast, under the present method, peak ranks rather than peak intensities may lead to an adequate model of spectra generation. Peak ranks have proven to be valuable for creating a scoring function for peptide identification. For example, InsPecT utilizes peak ranks in its scoring function. The following discussion shows how to utilize peak ranks in de novo peptide sequencing and to solve the corresponding PS problem.

A spectrum $s=s_1\ldots s_n$ is defined as a string in the alphabet I (ranks of peaks) and a peptide $\pi=\pi_1\ldots\pi_n$ as a string in the alphabet F (types of neutral losses). The probability of peptide r generating spectrum s is defined as $$Prob(s|\pi) = \prod_{i=1}^{n} Prob(s_i|\pi_i) \cdot \prod_{i=1}^{n} Prob(s_i|\pi_i^*),$$

where Prob(x|y) is an arbitrary |I|×|F| matrix representing the probability that a symbol y in the peptide generates a symbol x in the spectrum.

The spectrum strings $s=s_1\ldots s_n$ are generated from tandem mass spectra as follows: For simplicity, the top k peaks from every MS/MS spectrum are retained (k=150 in this implementation). Spectra are filtered to remove noisy peaks as follows: given a peak at mass M, retain the peak if it is among the top 5 peaks within a window of size 100 Da around M. For example, if this procedure gives t peaks, which are ranked from 1 to t, if t>k, keep only the top k peaks; if t<k, reinsert the top k-t peaks that were filtered out and assign them ranks t+1 to k. If the spectrum originally contains less than k peaks, peaks with lower ranks are generally at random positions in the spectrum to raise the total peak count to k. Define $s_i$ as the rank of the peak at mass i (if there is a peak at mass i) and define $s_i=0$ if there is no peak at mass i.

The peptide strings $\pi=\pi_1\ldots\pi_n$ are generated from amino acid sequences as follows: Define an alphabet of fragment ions as a set of integers corresponding to neutral losses, for example ion fragments b, (b−$H_2O$), and (b−$NH_3$) correspond to neutral losses {0, 18, 17}. Given a set of neutral losses $\{x_1\ldots x_t\}$, represent every amino acid of mass α as a string $s_1\ldots s_\alpha$ of length α with α-t zeros and t nonzero symbols 1, 2, ..., t located at positions α-$x_1$, α-$x_2$, ..., α-$x_t$. The peptide string $\pi=\pi_1\ldots\pi_k$ is simply a concatenation of strings corresponding to amino acids from the peptide. To make the model more accurate, the doubly charged b- and y-ions were added as additional types of ions generated by the peptide strings.

When applying the above model for peptide identification, the objective is to find the ratio of probabilities that a spectrum is generated by a given peptide $\pi$ relative to the probability that a spectrum generated by a string consists of all zeros (i.e., is noise). This can be represented as $$Prob(s|\pi)/Prob(s|0) = \prod_{i=1}^{n} Prob(s_i|\pi_i) / \prod_{i=1}^{n} Prob(s_i|0).$$

This can be further expressed as the sum of log-odds ratios:

$$\log\frac{\text{Prob}(s\mid\pi)}{\text{Prob}(s\mid0)} = \sum_{i=1}^{n}\log\frac{\text{Prob}(s_i\mid\pi_i)}{\text{Prob}(s_i\mid0)}$$

Using the training dataset described below, the values of log $$\frac{\text{Prob}(s_i\mid\pi_i)}{\text{Prob}(s_i\mid0)}$$

can be determined. The learning is performed separately for the lower and higher halves of the mass range. (Peaks corresponding to doubly charged ions only appear in the lower part of the spectrum.

A smoothing function was applied on these values for lower ranked peaks (11 to 150). For each ion type, the value at any rank was set to the average value in a window of five ranks around the given rank. The distribution of these values for each peak rank is shown in the tables in FIGS. 9a-9c for three different spectrum lengths—7, 8 and 20 (only ranks 1-10 are shown in the tables). While it is clear that these statistics vary with the length, the differences between adjacent lengths (e.g., 7 and 8) are typically small, as compared to differences between very different lengths (such as 7 and 20). Thus, specific length-dependent scoring can be applied using the approximate length inferred from the parent mass of the spectrum.

The MS-dictionary scoring function described herein can be validated by comparison against the scoring functions of the popular database search tools, X!Tandem and InsPecT. 50,000 spectra were chosen randomly from the *Shewanella* dataset and searched with SEQUEST, X!Tandem and InsPecT. Among the 50,000 spectra, 11,722 spectra had the same InsPecT and X!Tandem identifications, and only these were used in determining the correlation between InsPecT and X!Tandem. These spectra typically represent high InsPecT and X!Tandem scores; the correlation coefficient between the two methods for the whole range of scores would probably be lower. The score of the best peptide for each spectrum from database search was compared with the MS-dictionary score for the same spectrum peptide pair. As shown in FIGS. 9a-9c, there is good correlation between the MS-dictionary scoring function and the scoring functions used in the database search tools, the correlation coefficients being 0.87 for SEQUEST, 0.96 for InsPecT and 0.90 for X!Tandem. These correlations are even better than the correlation between InsPecT and X!Tandem raw scores themselves (correlation coefficient of 0.75).

Since the scoring function described above is additive, the dynamic programming algorithm for computing the generating function described above can be used. The number of peptide reconstructions is computed for each mass value, and the optimal score is determined for a mass within specified error tolerance from the parent mass ("ParentMass"). The top reconstructions are generated such that their TotalProbability adds up to a fixed threshold (for purposes of illustration, $10^{-9}$). Starting from the topmost score, reconstructions at each score are selected until their cumulative probability exceeds the threshold. All reconstructions at the borderline score are selected. Thus, the total probability may marginally exceed the threshold. The number of reconstructions generated for any spectrum is limited to at most 100,000.

The dynamic programming table is constructed for all mass values between 0 and (ParentMass+0.5), with a resolution of 0.1 Da. The number of reconstructions can be computed by summing the results for all mass values in a window of 1 Da around the exact ParentMass, to account for the low accuracy of ion-trap mass spectrometers. In case of precision mass spectrometry (e.g., FTMS), accurate solutions with low parent mass error can be obtained by increasing the resolution and reducing the size of the window around the ParentMass. For efficient computation, I and L are treated as the same amino acid, resulting in a 19-letter amino acid alphabet at the time the reconstructions are generated. In the low accuracy setting, Q and K are also treated as the same amino acid.

Some de novo reconstructions may be symmetric, i.e., the same peak in the spectrum may contribute to the score up to four times such as a singly or doubly charged b-ion or y-ion. While prior attempts to address this problem have proposed an anti-symmetric path approach, such an approach is not taken with the present method because (1) it can significantly increase the processing time to produce many reconstructions and (2) the high intensities from doubly-charged ions are not accounted for, but can significantly contribute to the MS-dictionary scores. To overcome this problem, the obtained peptide reconstructions can be rescored to exclude multiple contributions from the same peak. Starting with the highest scoring reconstructions, the peptide sequence is checked to determine if there are any peaks that have multiple contributions to the score. These peptides are rescored by using only the largest contributions from such peaks.

Recalibration of tandem mass spectra is important for correcting systematic mass errors. All existing spectral recalibration tools use templates (interpreted spectra with known b/y peaks) to perform linear recalibration using either least squares fit or least median of squares fit. In the de novo peptide sequencing framework, the reliable templates are hard to obtain, thus reducing the utility of spectral recalibration to QTOF and LTQ-FT data. In the low mass-accuracy setting, the applications of template based spectral recalibration are mainly limited to validating candidate peptide identifications. As a result, de novo peptide sequencing programs commonly default to a rather high fragment mass tolerance (e.g., 0.5 Da for ion-trap data) and thus result in many erroneous spectral interpretations. A template-free spectral recalibration procedure can be used for ion-trap mass spectra to reduce the required mass tolerance from 0.5 Da to 0.2 Da. In addition, this recalibration leads to significant improvement in MS-dictionary accuracy.

The fractional masses of amino acids may be as large as 0.1 for Arginine (mass 156.1 Da). The first step of an MS-recalibration tool is rescaling all peaks in the spectrum by multiplying all masses by 0.9995 to minimize the theoretical fractional masses of amino acids. After rescaling the fractional mass of Arginine is 0.02 (156.02 Da) and the fractional masses of all other amino acids are below 0.04 (the average fractional mass reduces threefold from 0.06 to 0.02).

Figure 17A:
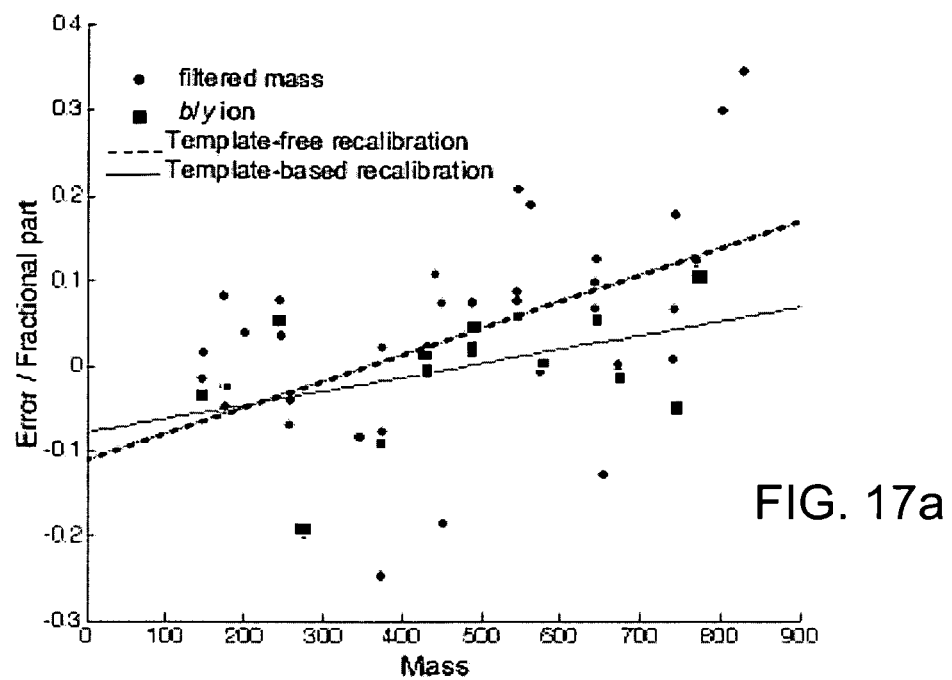
FIG. 17a is a plot showing a comparison of template-free and template-based recalibrations for a single spectrum.

MS-calibration further filters the rescaled spectra to retain the high intensity peaks using a sliding window as described above. Using "Int(m)" and "Frac(m)" to denote the integer and fractional part of mass m (respectively), the goal is to find $\alpha$ and $\beta$ minimizing the sum $(\text{Frac}(\alpha\cdot m+\beta))^2$ over all masses m in the rescaled filtered spectrum. FIG. 17a illustrates a comparison of template-free and template-based recalibrations for a single spectrum. Each square represents a 2-D point (m, Error (m)) for a b- or y-peak with mass m and the difference between the theoretical and experimental mass of the peak equal to Error (m) (for every b- and y-peak in the original spectrum.)

Figure 17B:
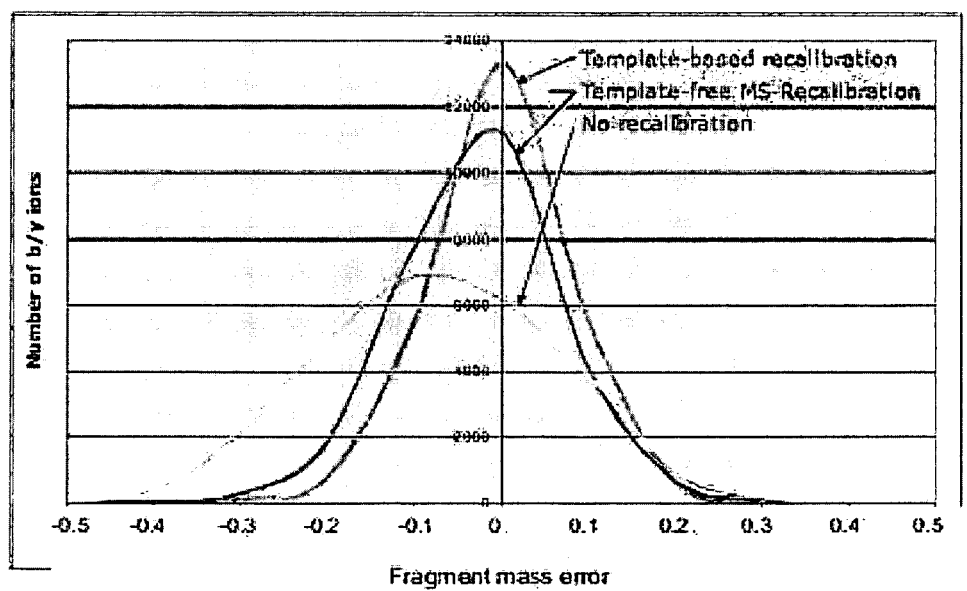
FIG. 17b is plot of MS-recalibration performance on sample spectra.

The coefficients $\alpha$ and $\beta$ are computed with the least squares fit algorithm and are used to recalibrate all peaks in the rescaled spectrum. While MS-recalibration has no information about the peptide that produced the spectrum, FIG. 17b shows that it achieves almost the same accuracy as the template-based approaches that recalibrate the spectra based on the information about the correct positions of b/y ions. FIG. 17b is a plot of the MS-recalibration performance on 1745 identified spectra of length 10 in the *Shewanella* dataset. The template-based recalibration uses the positions of theoretical b- and y-ions in the spectrum to fit the positions of b- and y-ions in the experimental spectrum using the least-squares fit algorithm. The template-free MS-recalibration does not require knowledge of the theoretical b- and y-ions. The error distribution for non-calibrated spectra is shown for comparison. The average error is 0.13 before recalibration, only 79% of b/y ions are within mass error 0.2 Da as compared to 96% after MS-recalibration (similar to 98% for the template-based recalibration.)

After applying MS-recalibration, one can safely set the mass tolerance to 0.2 Da (and retain 96% of b/y peaks) as compared to the 0.5 Da in existing approaches. Another advantage of the inventive method is that it centers the mass error distributions around zero regardless of their positions in the spectrum. This feature is important for creating a new scoring function that carefully accounts for errors in peak positions.

Most de novo peptide sequencing tools set up a fixed mass error threshold (e.g., 0.5 Da for ion-traps) then compute the scoring functions for all peaks within this error threshold. Assigning the same scores to all peaks within the error threshold may not be the optimal way to score spectra in both database search and de novo peptide sequencing applications. For example, a high intensity peak with mass error 0.5 Da is typically less "reliable" than a medium intensity peak with mass error 0.1. Recent incorporation of mass errors into the scoring function (as a quantitative component rather than a cut-off) led to a significant improvement in MSNovo accuracy. (L. Mo, et al., MSNovo: A Dynamic Programming Algorithm for de Novo Peptide Sequencing via Tandem Mass Spectrometry, *Anal. Chem.* 2007, 79:4870-4878) MS-dictionary also incorporates mass errors in the scoring functions and further improves the MS-Novo model as described below.

Figure 18A:
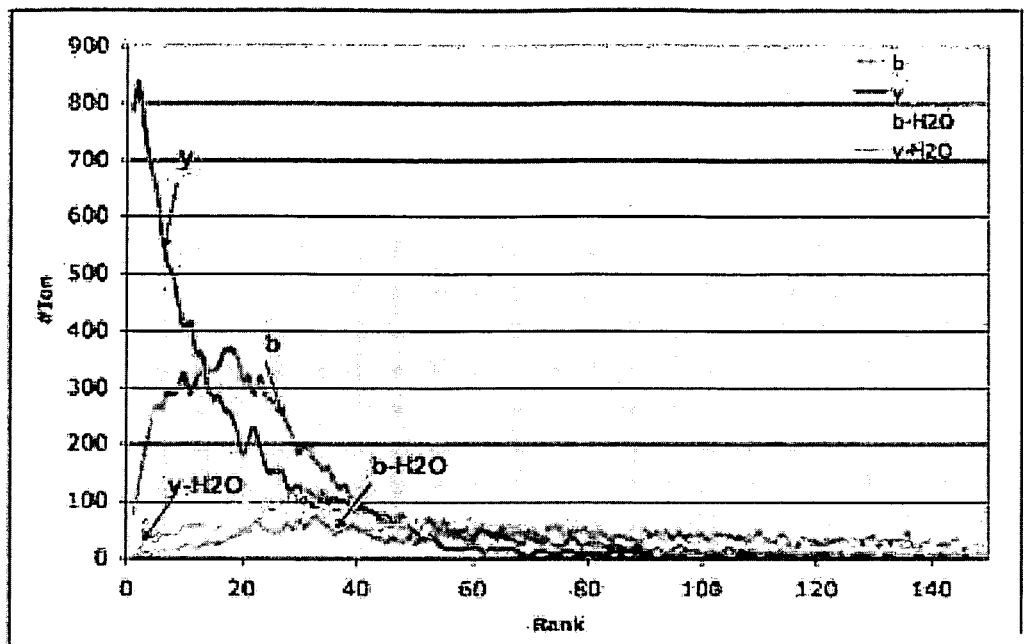
FIG. 18a is a plot of ion number versus rank, showing that different fragment ions have different rank distributions.
Figure 18B:
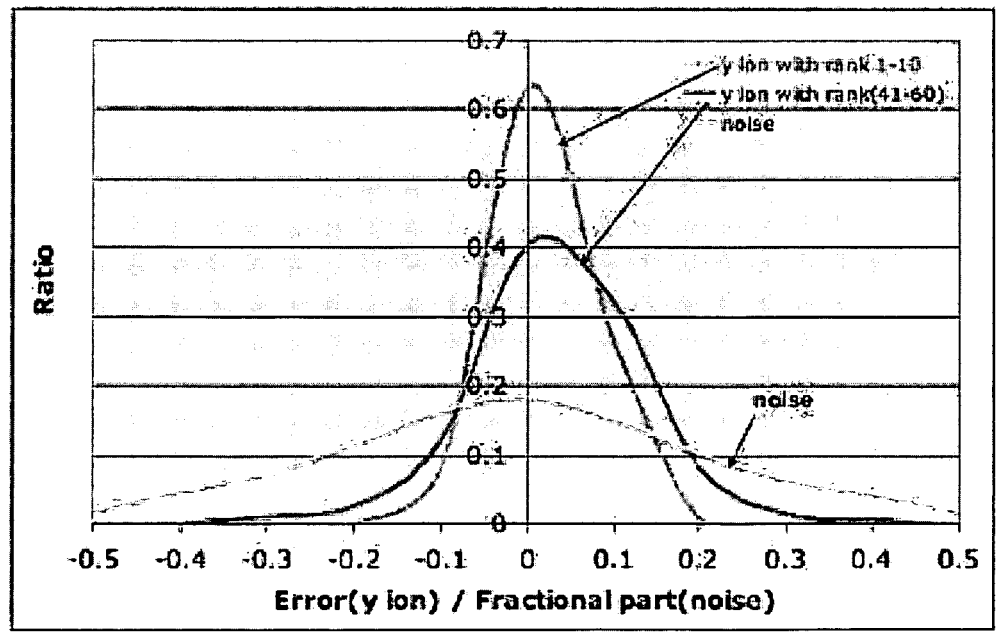
FIG. 18b is a plot showing correlation between peaks ranks and mass errors.

MSNovo used unified peak error model (Gaussian distribution) and peak rank model (exponential distribution) independent on the ion type, rank and position of each peak. However, FIG. 18a illustrates that different fragment ions have different rank distributions and, thus, different error models. FIG. 18b reveals that peak ranks and mass errors (that are assumed to be independent in MSNovo) are strongly correlated. High intensity peaks tend to have more accurate mass measurements than the lower intensity peaks. The fractional parts of very low intensity peaks (those ranking higher than 150) are centered around zero after rescaling.

FIG. 18b also reveals subtle irregularity in noise peaks indicating that the noise model in MSNovo needs to be adjusted. MS-dictionary takes these observations into account and incorporates the mass errors into its scoring function using a more adequate error model than used in MSNovo. The following provides a brief description of the error-dependent scoring for Boolean spectra. This model can be extended to MS/MS spectra as described above.

The Boolean spectra model assumes that a peptide symbol $\pi_i$ generates the spectrum symbol $s_i$ at exactly the same position. Extending this model, assume that the peptide symbol $\pi_i$ can generate spectrum symbol $s_{i+\epsilon}$, where $\epsilon$ represents a mass measurement error. Assume that errors are "small", i.e., they do not exceed a threshold $\epsilon_{max}$ ($\epsilon_{max}$ is typically 0.5 for ion-trap spectra). Incorporating errors into the spectrum generation model requires introducing the 3-dimensional matrix Prob(x,$\epsilon$|y), where $-\epsilon_{max} \leq \epsilon \leq +\epsilon_{max}$ and x and y are Boolean as before. The probability of peptide $\pi$ generating a spectrum s with error $\epsilon = \epsilon_1, \ldots, \epsilon_n$ can now be defined as $$\text{Prob}(s, \varepsilon | \pi) = \prod_{i=1}^{n} \text{Prob}(s_{i+\varepsilon_i} | \pi_i) \cdot \prod_{i=1}^{n} \text{Prob}(s_{i+\varepsilon_i}, \varepsilon_i | \pi_i).$$

The Peptide Sequencing Problem can now be reformulated as follows:

Peptide Sequencing Problem with Errors.

Given a spectrum s and a DAG G, find a G-peptide $\pi$ and mass errors $\epsilon$ maximizing Prob(s,$\epsilon$|$\pi$) over all G-peptides and over all mass errors $\epsilon$.

The matrix Prob(x,$\epsilon$|y) was learned from the training sample and the learned parameters were further used in the dynamic programming algorithm as described before. Table 2 compares the performance of MS-dictionary with PepNovo version 1.03 and illustrates that MS-dictionary outperforms PepNovo for all peptide lengths.

TABLE 2

| Length | % correct amino acids | | % correct peptides | |
|---|---|---|---|---|
| | PepNovo | MS-dictionary | PepNovo | MS-dictionary |
| 8 | 88.7 | 92.2 | 51.1 | 58.1 |
| 10 | 85.8 | 91.2 | 38.2 | 49.6 |
| 12 | 79.7 | 87.2 | 23.1 | 34.5 |
| 14 | 71.1 | 81.7 | 11.8 | 17.8 |
| 16 | 61.1 | 79.0 | 3.8 | 12.9 |
| 18 | 56.8 | 74.2 | 1.5 | 7.6 |
| 20 | 49.8 | 65.6 | 0.3 | 3.3 |

Example 2

De Novo Reconstructions Using *Shewanella* Datasets

The spectra dataset for computing the probabilities of peak ranks for various ions types was obtained from *Shewanella oneidensis* MR1, described above in Example 1. The spectra and identifications from this dataset were acquired on an ion-trap MS (LCQ, ThermoFinnegan, San Jose, Calif.) using electrospray ionization (ESI). The program extract.msn (ThermoFinnegan) was used to generate the dta files with standard options. The 28,377 peptides were reliably identified with false discovery rate 5% using InsPecT (spectrum-level FDR is 1%). An InsPecT search was run using default parameter settings (fragment ion tolerance of 0.5 Da and parent mass tolerance of 2.5 Da). For this study, 21,087 tryptic peptides with charge 2 were selected. One representative spectrum was obtained for each of these peptides (most peptides were identified from multiple spectra). They were then grouped by the length of their peptide identifications to form a test dataset for each length. Here, the length of the InsPecT identification of a spectrum is referred to as the "spectrum length". For the sake of convenience, lengths 7 through 10 and even lengths between 10 and 20 were considered. The trends across these lengths, as shown in the results, show smooth progression and there is no reason to believe that the odd lengths between 10 and 20 would show any deviant behavior. To avoid computational artifacts introduced by errors in the parent mass, the parent masses were corrected according to the InsPecT identification.

Figure 11A:
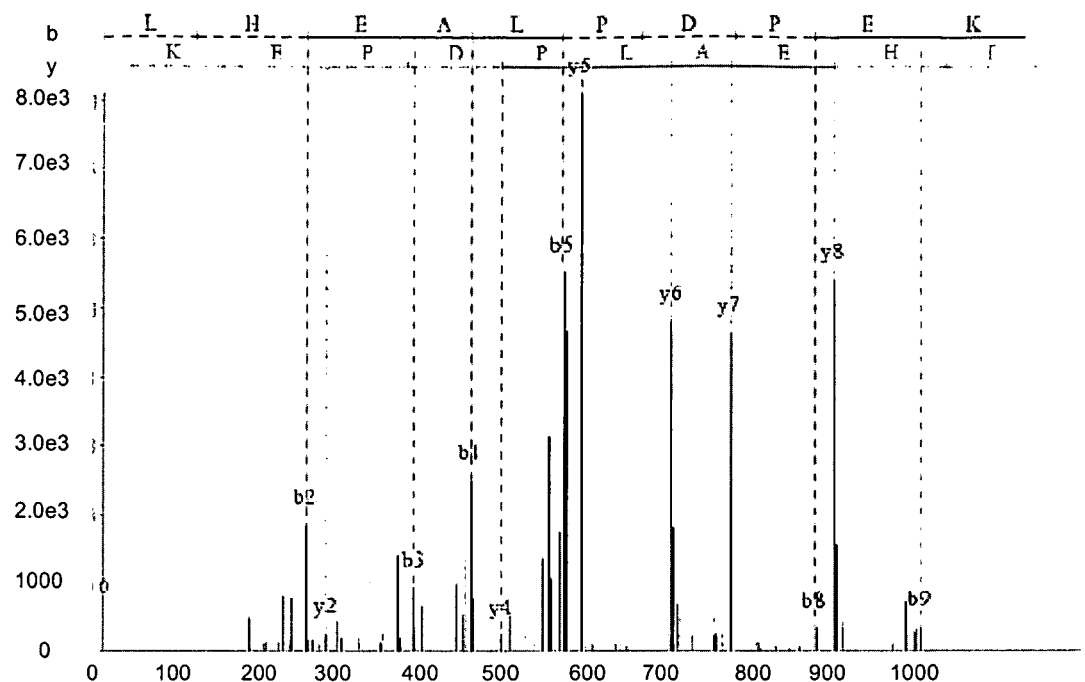
FIGS. 11a and 11b show two optimal de novo interpretations for a particular spectrum.
Figure 11B:
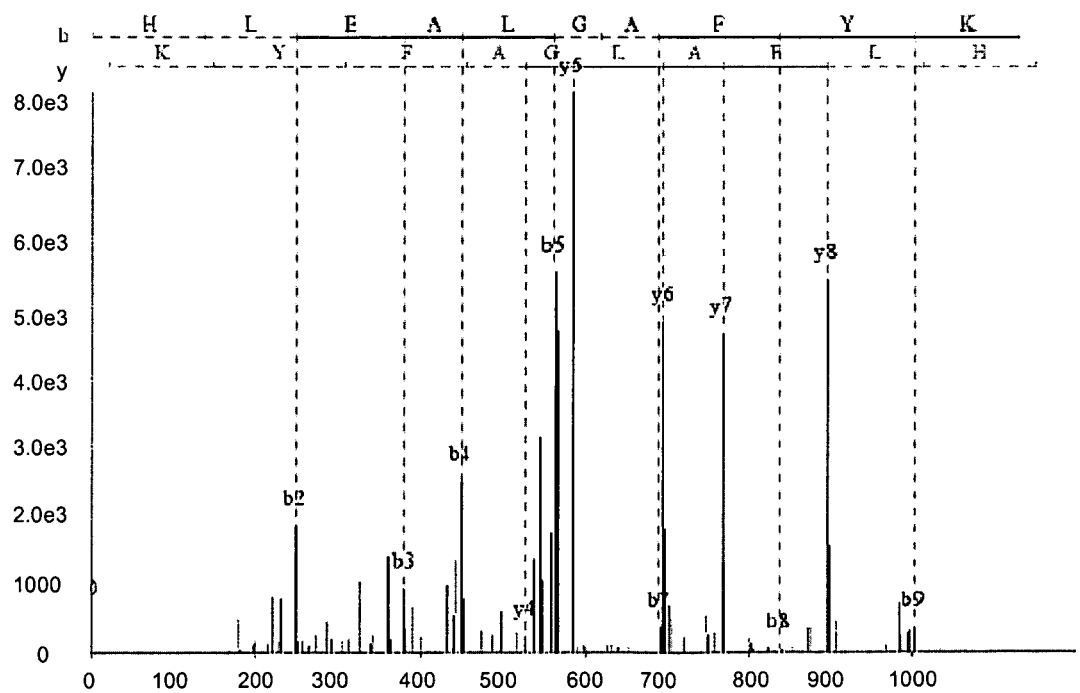
Figure 12A:
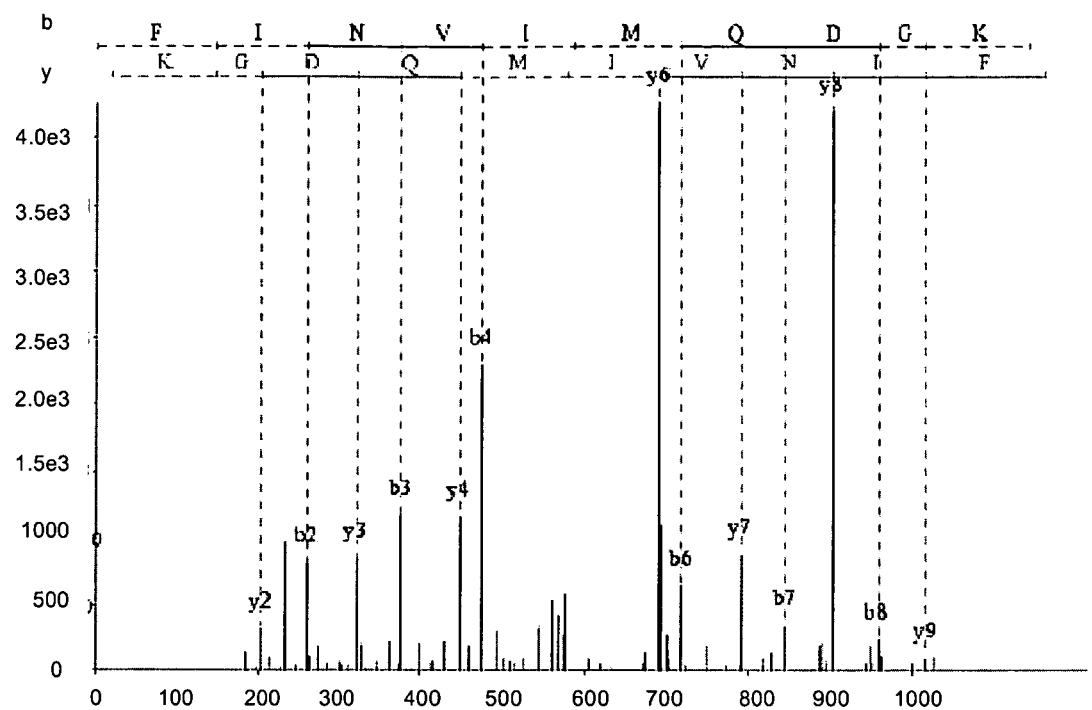
FIG. 12a shows a peptide identified in a database search and FIG. 12b shows a de novo reconstruction for a particular spectrum.
Figure 12B:
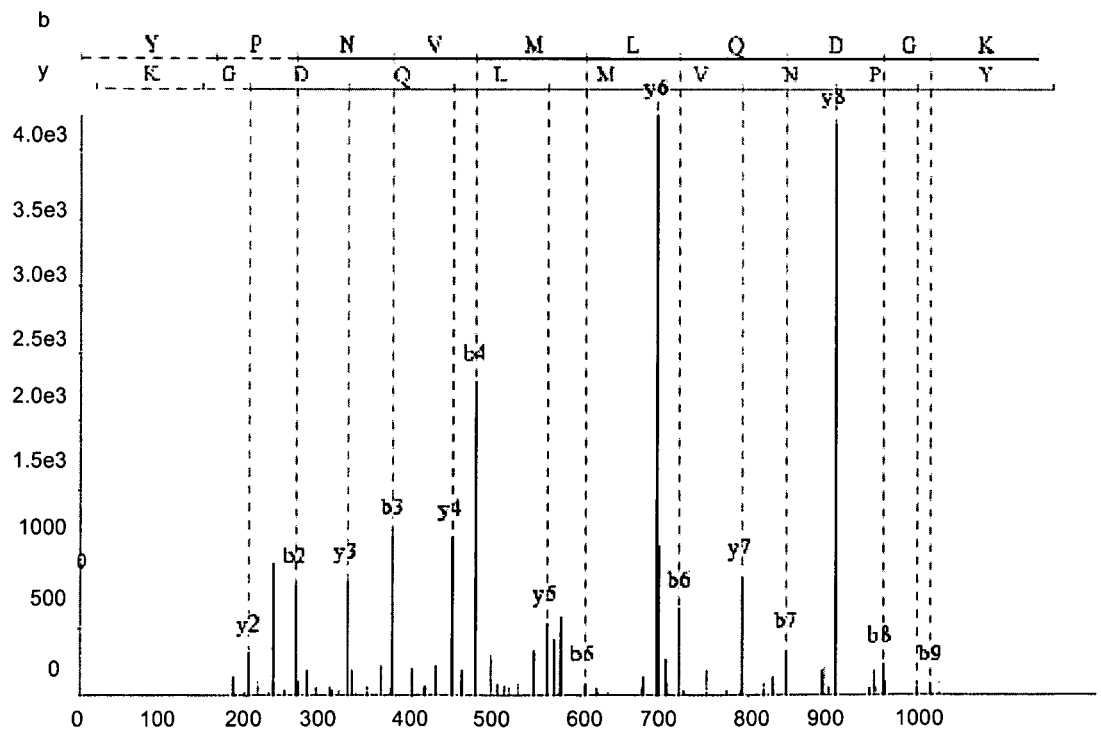
Figure 13:
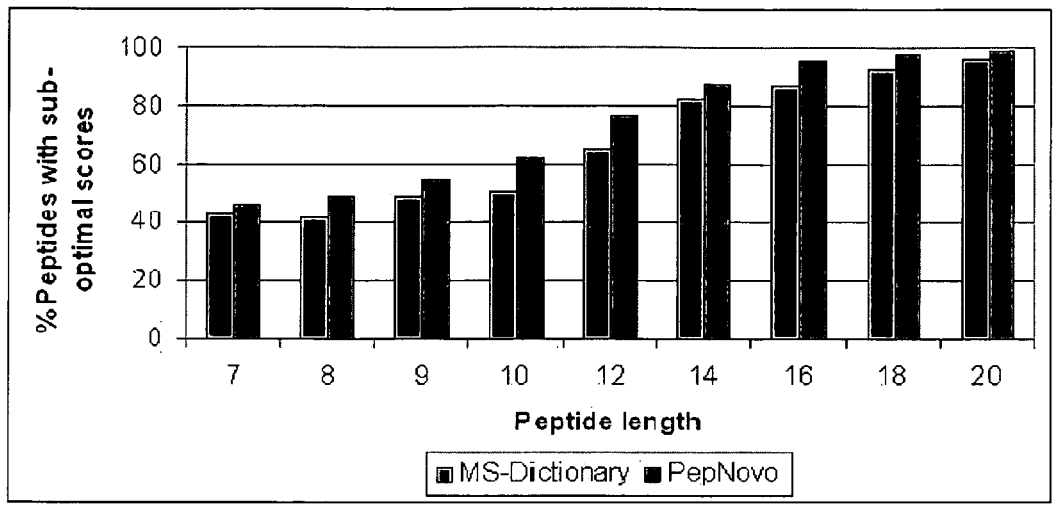
FIG. 13 is a histogram showing fraction of the test spectra of length 10 for which the correct peptide has a sub-optimal de novo score.

A spectrum may have many reconstructions with the optimal score, and in these cases, reporting only one reconstruction is clearly deficient. For example, FIGS. 11a and 11b show a spectrum for which two very distinct peptides, LHEALPDPEK and HLEALGAFYK, receive the optimal score of 90. Furthermore, even generating all optimal reconstructions may not be sufficient to find the correct peptide. For some spectra, the correct peptide may have a lower score than an incorrect peptide. FIGS. 12a and 12b show a spectrum for which the correct peptide FINVIMQDGK (as identified reliably by a database search with InsPecT) has score of 111, while another possible reconstruction YPNVMLQDGK (not present in the database) has a higher score of 123. For about 60% of length 10 spectra, the correct peptide has a suboptimal PF-Novo score (~50% for MS-dictionary score), and this fraction quickly increases with peptide length 20 (See FIG. 13). Since the existing de novo approaches fail to identify the correct peptide as the optimal reconstruction in a large fraction of the spectra, a de novo method should consider multiple reconstructions with suboptimal scores.

Even a database search method, if it were searching in the database of all possible peptides, would fail to identify the correct peptide for more than half of the length 10 spectra that were correctly identified in the real protein database. Since actually searching a database of all peptides is practically infeasible, this failure rate is conservatively estimated by creating a custom database for each spectrum containing all de novo reconstructions with MS-dictionary scores better or equal to the correct peptide. Even if one were to use the theoretical database of all possible peptides, it is very likely that the identified peptides would be one of those top reconstructions included in the custom database. The rate of finding the correct peptide would only drop if more peptides were added. InsPecT was able to identify the correct peptide on such custom database in only 42% of the cases and X!Tandem in 35% cases for length 10 peptides. Both InsPecT (version 2006.09.07) and X!Tandem (version 2007.01.01.2) were run with parent mass tolerance of 2.5 Da, fragment mass tolerance of 0.5 Da, fixed modification of C+57, no optional modifications and without any enzyme preference. The best match for each spectrum is reported. The parent masses of spectra were corrected according to the mass of the correct peptide. Table 3 illustrates that the accuracy of various tools decreases sharply with the increase in the spectrum length. PepNovo (a de novo search method) has similar or better accuracy than InsPecT in finding the correct peptide reconstruction. PepNovo version 1.03 was used with fixed C+57 modification.

TABLE 3

| Length | InsPecT | X!Tandem | PepNovo | MS-dictionary |
|--------|---------|----------|---------|---------------|
| 7      | 63      | 51       | 54      | 57            |
| 8      | 59      | 47       | 51      | 58            |
| 9      | 48      | 41       | 45      | 51            |
| 10     | 42      | 35       | 38      | 50            |
| 12     | 18      | 22       | 23      | 35            |
| 14     | 16      | 11       | 12      | 18            |

Figure 14:
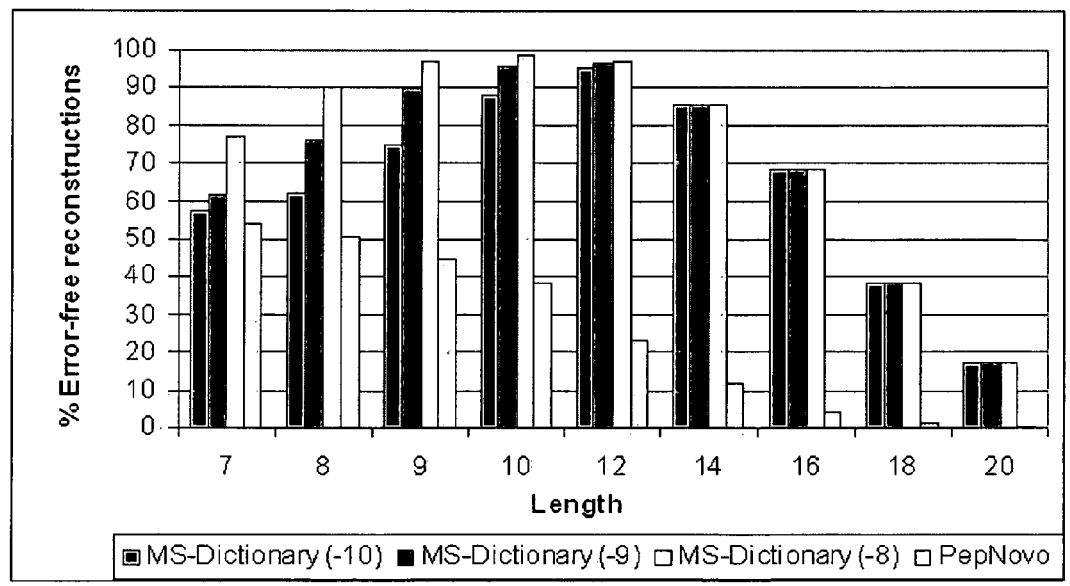
FIG. 14 is a histogram showing the MS-dictionary accuracy as a function of spectrum length.

In some applications (e.g., searches in large EST databases or using MS/MS for proteogenomic annotations), the databases can be very large. This implies that searching in such databases (at least for shorter peptides) is not unlike the search in the database of all peptides. Table 3 leads to a surprising conclusion that for short peptides, simply generating de novo reconstructions and matching them against the database may be a more accurate (and faster) approach than X!Tandem/InsPecT in case of very large databases. Below it will become apparent that MS-dictionary provides better performance than InsPecT/X!Tandem/PepNovo in such applications (FIG. 14).

The test datasets with known identifications in *Shewanella* were analyzed using the MS-dictionary for each peptide length. The test datasets (all peptide identifications in *Shewanella*) were analyzed with MSDictionary for each peptide length. The size of the spectral dictionary depends on the TotalProbability parameter of the generating function that influences the error rate of peptide identifications if the spectrum was submitted to a database search. Since the test set is tryptic peptides, only reconstructions that end in K or R are considered. It should be noted that this is an example only, and MS-dictionary is not limited to tryptic peptides.

As the spectrum length increases, the size of the peptide search space increases dramatically, making it harder to generate the spectral dictionary. Thus all de novo search methods yield lower accuracy for longer peptides. The generating function approach allows one to dynamically determine the number of peptide reconstructions and increase the chance of finding the correct peptide in the set of de novo reconstructions (see FIG. 15).

The number of reconstructions obtained for these same-length spectra varies over orders of magnitude. While the peak of the distribution of the number of reconstructions is at log 2 (size of spectral dictionary)≈10, some of these spectra have fewer than 100 or more than 10,000 reconstructions. This remarkable variance in the size of spectral dictionaries illustrates the point that different spectra have different number of good reconstructions. This consideration should be taken into account by de novo methods that only return a fixed number of peptides.

Recently, de novo peptide sequencing for data acquired from FT-ICR instruments has been described where both the parent mass and the peak positions are accurate. Acquiring such spectra remains time-consuming, and an intermediate approach that is gaining prominence is to acquire mass spectra with high precision at MS1 stage and lower precision at MS/MS stage, giving accurate parent mass but inaccurate peak positions. However, the existing de novo search methods are aimed toward ion traps or other low accuracy mass spectrometers, which may have parent mass errors on the order of 1 Dalton. Since vertices in the spectrum graph are constructed based on low accuracy peaks, it is not clear how to exploit the accurate parent mass information that is available from new high accuracy instruments. Availability of accurate Parent-Mass values can be effectively utilized in MS-dictionary to filter the reconstructions. The number of reconstructions for 5 ppm accuracy is typically 416 times smaller than the corresponding numbers for 0.5 Dalton accuracy (data are not shown).

In any database search, a large number of spectra are expected to remain unidentified. This may happen due to several reasons: these spectra may have many missing or noisy peaks making them difficult to interpret, the corresponding peptide may not be present in the database or the peptide may have a posttranslational modification not captured by the search algorithm. In case of *Shewanella oneidensis* MR1, only ≈10% of the 14.5 million spectra were reliably identified. In contrast, MS-dictionary is able to find identifications for some previously unidentified spectra by searching the six-frame translation of the *Shewanella* genome (rather than the protein database).

All spectra from *Shewanella* that were not identified in the database search, with the ParentMass range from 1100 to 1200 Da (the typical mass range for length 10 peptides) were selected. From these, a further selection of 24,814 spectra with high de novo scores (above 50) was made. Peptide reconstructions were generated for these spectra, at three different values of TotalProbability. The same analysis was repeated with a decoy database of the same size. A spectrum is considered identified if any of the reconstructions is present in the six-frame translation of the *Shewanella* genome (target database). Table 4 shows the number of new peptides identified by the MS-dictionary in each database that were not found in the earlier database search.

TABLE 4

| Total-Probability | IDs (target) | IDs (decoy) | FDR | New Peptides |
|---|---|---|---|---|
| 1e−9 | 1169 (8771) | 29 (64) | 0.025 | 768 (746) |
| 1e−10 | 995 (6171) | 6 (6) | 0.006 | 652 (646) |
| 5e−11 | 914 (5327) | 2 (2) | 0.002 | 595 (591) |
| 2e−11 | 794 (4269) | 0 (0) | 0 | 514 (512) |

For TotalProbability=$10^{-10}$, 1007 new peptides are identified from 6211 spectra in the target database, while only 6 peptides (from 6 spectra) are identified in the decoy database, corresponding to a peptide level false discovery rate of 0.6%. As the TotalProbability is lowered, the false discovery rate becomes zero at $2\times10^{-11}$ with 794 peptide identifications. 280 of the identifications were previously identified by InsPecT (from other higher quality spectra), but 514 represent new peptide identifications. Interestingly, 512 (99.6%) of the identifications map to the known protein sequences (including contaminants), providing further confirmation that these identifications are correct. Indeed, since the size of the *Shewanella* protein database is only ≈15% of the size of six-frame *Shewanella* translation, one expects that only 15% of these proteins would hit the *Shewanella* database by chance. Moreover, out of 512 peptides, 508 are matched to expressed proteins (confirmed by at least two InsPecT identifications) and 2 are matched to proteins with a single identified peptide, confirming the expression of these proteins.

A closer look at the two peptides that fall outside the annotated proteins reveals two frame-shifts. The first peptide, IAVGLSSANFGR, maps downstream of the gene SO_2754 which is annotated as "hypothetical sodium-type flagellar protein MotY", and has length 122 aa. A BLAST query of the peptide against other *Shewanella* strains shows that the peptide is conserved in four other strains and contained in longer proteins of length 289. Alignment of the nucleotide sequence of *Shewanella oneidensis* MR1 against these other strains reveals a sequencing error (insertion of an extra A at nucleotide position 362) that results in a stop codon and early truncation of the gene with only 122 amino acids. The second peptide, SDIGWGSQIR, falls in the region of the gene SO_0991 (peptide chain release factor 2) which is now annotated in TIGR (The Institute for Genomic Research, now JCVI (J. Craig Venter Institute)) as a programmed frameshift (but has the correct protein sequence missing from FASTA files because of the frameshift). These examples show that new peptide identifications from MS-dictionary not only increase coverage for annotated genes but also provide clues for correcting gene annotations.

It should be noted that the peptide identifications reported here based on the spectra in 1100 to 1200 Da ParentMass range only, and their number is expected to be much larger if spectra of other masses are also included. Other data indicate that spectra in lower and higher mass ranges also show similar trends as spectra in the 1100 to 1200 Da range. MS-dictio-nary, thus, has the potential to provide a significant number of new peptide identifications from spectra that were missed using traditional database searches.

While mass spectrometry methods have been successfully used for bacterial gene predictions, the proteogenomic studies of large eukaryotic genomes are still in their infancy. Even the fastest MS/MS database search tools become impractical in such studies since they require searches in huge databases resulting from the 6-frame translations of eukaryotic genomes (≈2.5 billion amino acids for repeat-masked human genome). While the recent discovery of nearly 1000 new genes in the human genome emphasized the need for proteogenomic annotations, it is not clear how to scale the traditional MS/MS tools to enable searches in the translated eukaryotic genomes. A step toward proteogenomic searches of human genome has been made by combining EST and MS/MS analysis. While this approach is very valuable, it can only be successful if the same exons are supported by both EST and MS/MS data. The largest proteogenomic analysis conducted so far is the search of the six-frame translation of *Arabidopsis thaliana*, which resulted in the discovery of nearly 500 new genes using InsPecT. While InsPecT is 10 times faster than X!Tandem and 60 times faster than SEQUEST, even it is too slow in searches of the translated mammalian genomes. Since both InsPecT and X!Tandem report unexpected errors on the translated human genome and, therefore, have been deemed incapable of searching the translated human genome, InsPecT was run on a 124 times smaller database. It was assumed that its running time would be proportional to the database size. The running time of InsPecT is estimated at 42 seconds per spectrum (a lower bound that does not account for overhead caused by indexing/partitioning of large databases), while MS-dictionary takes less than 1 second per spectrum on average on a standard desktop computer with 2.16 GHz INTEL® processor. As described in the following, MS-dictionary can search the translated human genome and identify over 10,000 human peptides with low FPR. Recently, it was shown that such peptides can significantly improve the accuracy of traditional de novo gene prediction tools and boosted the accuracy of GeneID predictions by 0.65 correct exons per gene on average.

The inventive MS-dictionary generates the spectral dictionary for each spectrum and uses fast pattern matching to match the spectral dictionary against the indexed database. (Indexing the entire 6-frame translation of the human genome takes less than an hour.) A simple partitioning/indexing was used to divide the translated human genome into 124 equally sized sub-genomes. Generating a spectral dictionary with 10,000 reconstructions takes 0.1 second per spectrum. Pattern matching of a spectral dictionary against all 124 databases (including I/O overhead) takes 0.8 seconds per spectral dictionary on average. This results in less than 1 second running time, a 40-fold improvement over InsPecT. It is estimated that optimized indexing/partitioning or executing MS-dictionary on a large shared memory machine would further reduce the running time.

To benchmark MS-dictionary, a human embryonic kidney 293 (HEK293) MS/MS dataset was used. (See, e.g., Tanner, Improving gene annotation using peptide mass spectrometry, *Genome Res.*, 2007,17:231-239.) 48,926 doubly-charged peptides with tryptic C-terminus identified by InsPecT were selected for the study.[10] (InsPecT version 20070613, human IPI database version 3.18) with 2.5% false discovery rate). (While the MS-dictionary generates both tryptic and nontryptic peptides, doubly-charged peptides with tryptic C-terminus were selected to simplify benchmarking.) The 17,821 peptides that span the exon boundaries were removed (these peptides cannot be identified by searching the translated human genome), resulting in 31,105 peptides. Since most peptides in HEK293 are represented by multiple spectra, one spectrum was randomly selected out of all spectra of the same peptide. The 31,105 spectra were further searched against the translated human genome using Ensembl Release 48 (ensembl.org) with masked repeats and with corrected parent mass as described previously. For each spectrum, a spectral dictionary was generated with TotalProbability=$10^{-11}$, limiting the maximum size of the spectral dictionaries to 10,000. Each peptide in the spectral dictionary was matched (without errors) against the translated human genome.

Searches in the translated human genome are not expected to identify all spectra reliably identified in the human protein database. Indeed, losses have been reported of about 30% of all identifications of peptides falling within exons after switching from the protein database to the translated genome database of *Arabidopsis thaliana*. Such losses seem to be unavoidable because many reliable identifications in the protein database end up being statistically insignificant identifications in the much larger translated genome. For example, while the TotalProbability=$10^{-10}$ makes sense for searching the human protein database, it results in very high error rates (FPR=25%) in a ≈100 times larger translated human genome. Therefore, all peptide identifications with TotalProbability≥$10^{-10}$ will be lost after switching from the protein database to the translated human genome. In particular, all peptides of length 8 and shorter are likely to be lost since TotalProbablity even of a single peptide of length 8 is rather high (≈$0.4 \cdot 10^{-10}$). TotalProbablity=$10^{-11}$ was chosen as a threshold resulting in estimated FPR= DatabaseSize·TotalProbability=$2.5 \cdot 10^9 \cdot 10^{-11}$=0.025. Since 9,470 out of 31,105 peptides (30%) have TotalProbability exceeding $10^{-11}$, they cannot be identified in any sensible database search against the translated human genome. This leaves 21,635 peptides that can be potentially identified in the translated human genome.

The MS-dictionary identified 10,266 out of 21,635 spectra in the translated human genome. 98.9% of the identified peptides fall into the human proteins and only 1.1% fall into non-coding regions. While most spectral dictionaries have zero or one hit in the human genome, 1.8% of them have multiple hits (typically 2 hits). To further estimate FPR, out of a single run of 25,746 spectra, unidentified doubly-charged spectra were selected (16,205 spectra). The MS-dictionary was then used to generate spectral dictionaries and match them against the translated human genome. MS-dictionary identified only 71 spectra in this experiment, corresponding to FPR 0.44%.

Therefore, MS-dictionary reliably identifies ≈10,000 peptides from human proteins without knowing the human proteome. However, it also "loses" ≈11,000 peptides that can be potentially identified in searches of the translated human genome.

Figure 15:
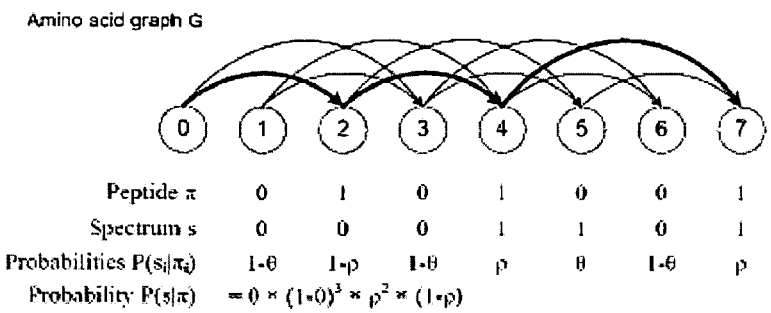
FIG. 15 is an amino acid graph G for all peptides with a parent mass 7 and only two possible amino acids A and B.
Figure 16:
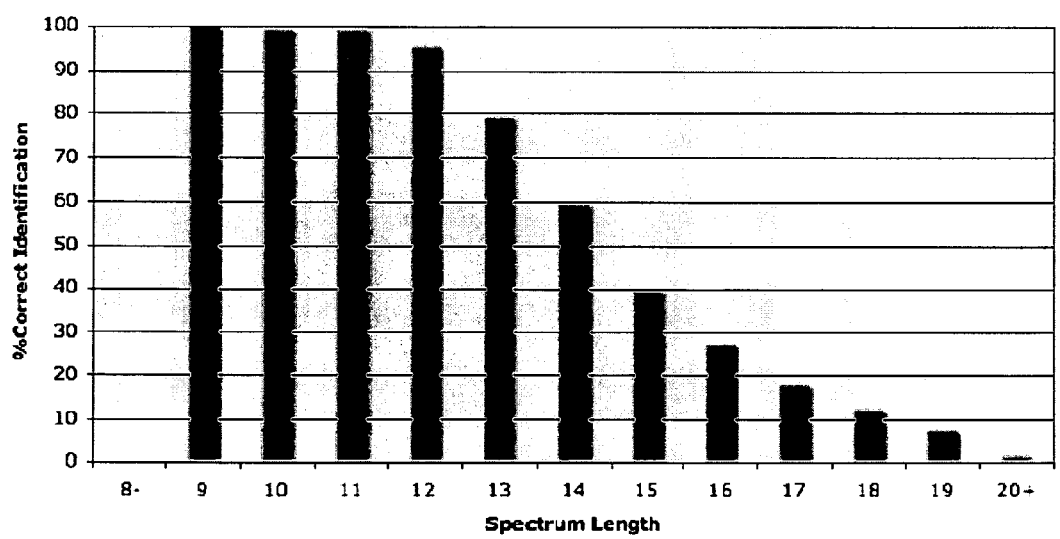
FIG. 16 is a histogram showing the percentage of peptides identified by MS-dictionary in the translated human genome.

FIG. 15 illustrates that while the inventive MS-dictionary identifies a large fraction of peptides of length 1013, the performance tends to deteriorate for shorter and longer peptides. Since the TotalProbability threshold needs to be low in proteogenomic applications, only very high quality spectra of shorter peptides represent reliable identifications (only 23% of spectra of length 9). This does not mean that MS-dictionary performs poorly, but rather reflects the stringent threshold that is applied. For the spectra of length more than 14 aa, the performance of the MS-dictionary deteriorates because of the limited size of spectral dictionaries. Further, algorithmic developments (e.g., generating dictionaries of long tags) are needed to address this issue.

The foregoing description demonstrates the importance of obtaining multiple peptide reconstructions for a spectrum, particularly in the context of a de novo search. The number of generated reconstructions must not be fixed a priori, as done by existing de novo tools, but should be decided dynamically for the given spectrum since the number of good quality reconstructions varies for each spectrum. According to the present invention, a dynamic programming algorithm based on the generating function in statistical physics has been created to allow the number of reconstructions to be counted for each score, and accordingly, determine the set of reconstructions that must be reported. This method is capable of using the high precision spectra for obtaining identifications with low ppm error in parent mass. The scoring function uses a generalized model of peak ranks for different ions types that scales well for longer peptide lengths.

The ability to generate spectral dictionaries makes the inventive method particularly useful for hybrid de novo based database search, by increasing the likelihood of finding the correct peptide while keeping the number of false identifications low. The MS-dictionary identifies new peptides from spectra that were not identified using a regular database search. Further, the MS-dictionary can be modified to search for mutations and polymorphisms by simply substituting the exact pattern matching by error-tolerant pattern matching of spectral dictionaries against databases. Possible applications of this hybrid approach include use as a tool for peptide identification by extending it to highly-charged spectra and improving the efficiency of this approach in case of longer peptides. Deteriorated performance for highly-charged and long peptides is an important limitation of all de novo approaches to spectral interpretations. The existing de novo peptide sequencing tools are aimed at charge 2 peptides with the single exception of GBST algorithm that is best suited for tag generation rather than full length de novo peptide sequencing. All tools were found to deteriorate while searching longer peptides in very large databases. For example, InsPecT and X!Tandem would correctly identify only 16% and 11% of all length 14 peptides in the de novo peptide sequencing framework (Table 3). While the inventive MS-Dictionary improves on these tools, its accuracy is also rather low (18%). This observation reveals the shortcomings of existing de novo and database search tools that often score the incorrect peptides higher than the correct peptides. The "homeometric peptides" have been identified as a key obstacle for developing better de novo algorithms—they become more pronounced with the increase in the peptide length. This problem can be partially alleviated by generating all reconstructions with a given TotalProbability and further matching them against a database (FIG. 14).

REFERENCES

Nesvizhskii, A.; Vitek, O.; Aebersold, R. Analysis and validation of proteomic data generated by tandem mass spectrometry. *Nature Methods* 2007, 4, 787-797.

Kall, L.; Storey, J.; Maccoss, M.; Noble, W. Assigning significance to peptides identified by tandem mass spectrometry using decoy databases. *J. Proteome Res.* 2008, 7, 29-34.

Can, S.; Aebersold, R.; Baldwin, M.; Burlingame, A.; Clauser, K.; Nesvizhskii, A. The Need for Guidelines in Publication of Peptide and Protein Identification Data:

Working Group On Publication Guidelines For Peptide And Protein Identification Data. *Mol Cell Proteomics* 2004, 3, 531.

Bradshaw, R.; Burlingame, A.; Carr, S.; Aebersold, R. Reporting Protein Identification Data: The next Generation of Guidelines. *Mol Cell Proteomics* 2006, 5, 787-8.

Keller, A.; Nesvizhskii, A.; Kolker, E.; Aebersold, R. Empirical statistical model to estimate the accuracy of peptide identifications made by MS/MS and database search. *Anal Chem* 2002, 74, 5383-5392.

Sadygov, R.; Yates, J. A hypergeometric probability model for protein identification and validation using tandem mass spectral data and protein sequence databases. *Anal Chem* 2003, 75, 3792-3798.

Geer, L.; Markey, S.; Kowalak, J.; Wagner, L.; Xu, M.; Maynard, D.; Yang, X.; Shi, W.; Bryant, S. Open mass spectrometry search algorithm. *J. Proteome Res* 2004, 3, 958-964.

Altschul, S.; Gish, W.; Miller, W.; Myers, E.; Lipman, D. Basic local alignment search tool. *J. Mol. Biol* 1990, 215, 403-410.

Elias, J.; Gygi, S. Target-decoy search strategy for increased confidence in large-scale protein identifications by mass spectrometry. *Nature Methods* 2007, 4, 207-214.

Fenyo, D.; Phinney, B.; Beavis, R. Determining the overall merit of protein identification data sets: rho-diagrams and rho-scores. *J Proteome Res* 2007, 6, 1997-2004.

Higdon, R.; Hogan, J.; Belle, G.; Kolker, E. Randomized sequence databases for tandem mass spectrometry Peptide and protein identification. OMICS 2005, 9, 364-79.

Higgs, R.; Knierman, M.; Freeman, A.; Gelbert, L.; Patil, S.; Hale, J. Estimating the statistical significance of peptide identifications from shotgun proteomics experiments. *J Proteome Res* 2007, 6, 1758-1767.

Beausoleil, S.; Jedrychowski, M.; Schwartz, D.; Elias, J.; Villen, J.; Li, J.; Cohn, M.; Cantley, L.; Gygi, S. Large-scale characterization of HeLa cell nuclear phosphoproteins. *Proceedings of the National Academy of Sciences* 2004, 101, 12130-12135.

Qian, W.; Liu, T.; Monroe, M.; Strittmatter, E.; Jacobs, J.; Kangas, L.; Petritis, K.; Camp, D.; Smith, R. Probability-based evaluation of peptide and protein identifications from tandem mass spectrometry and SEQUEST analysis: the human proteome. *J Proteome Res* 2005, 4, 53-62.

Waterman, M.; Vingron, M. Rapid and Accurate Estimates of Statistical Significance for Sequence Data Base Searches. *Proceedings of the National Academy of Sciences of the United States of America* 1994, 91, 4625-4628.

Fenyo, D.; Beavis, R. A method for assessing the statistical significance of mass spectrometry-based protein identifications using general scoring schemes. *Anal. Chem* 2003, 75, 768-774.

Eriksson, J.; Chait, B.; Fenyo, D. A statistical basis for testing the significance of mass spectrometric protein identification results. *Anal. Chem.* 2000, 72, 999-1005.

Eng, J.; McCormack, A.; Yates, J. An Approach to Correlate Tandem Mass-Spectral Data of Peptides with Amino Acid Sequences in a Protein Database. *Journal Of The American Society For Mass Spectrometry* 1994, 5, 976-989.

Perkins, D.; Pappin, D.; Creasy, D.; Cottrell, J. Probability-based protein identification by searching sequence databases using mass spectrometry data. *Electrophoresis* 1999, 20, 3551-3567.

Tanner, S.; Shu, H.; Frank, A.; Wang, L.; Zandi, E.; Mumby, M.; Pevzner, P.; Bafna, V. InsPecT: identification of post-translationally modified peptides from tandem mass spectra. *Anal Chem* 2005, 77, 4626-4639.

Nagarajan, N.; Jones, N.; Keich, U. Computing the P-value of the information content from an alignment of multiple sequences. *Bioinformatics* 2005, 21, i311-i318.

Graham, R.; Knuth, D.; Patashnik, O. *Concrete mathematics: a foundation for computer science*; Addison-Wesley Longman Publishing Co., Inc. Boston, Mass., USA, 1989.

Wilf, H. *Generatingfunctionology*.; Academic Press, Boston, Mass., 1994.

Pathria, R. *Statistical Mechanics, 2nd edition*; Butterworth-Heinemann, Oxford, 1996.

Tsur, D.; Tanner, S.; Zandi, E.; Bafna, V.; Pevzner, P. Identification of post-translational modifications via blind search of mass-spectra. *Nature Biotechnology* 2005, 23, 1562-2567.

Bandeira, N.; Tsur, D.; Frank, A.; Pevzner, P. Protein Identification via Spectral Network Analysis. *Proceedings of the National Academy of Sciences* 2007, 104, 6140-6145.

Bandeira, N.; Olson, J.; Mann, M.; Pevzner, P. De Novo Peptide Sequencing via Multi-Stage Mass Spectrometry. *Bioinformatics (in press)*.

Kim, S.; Gupta, N.; Bandeira, N.; Pevzner, P. Spectral dictionaries: Integrating de novo peptide sequencing with database search of tandem mass spectra. Submitted.

Taylor, J.; Johnson, R. Implementation and uses of automated de novo peptide sequencing by tandem mass spectrometry. *Anal Chem* 2001, 73, 2594-2604.

Dancik, V.; Addona, T.; Clauser, K.; Vath, J.; Pevzner, P. De novo peptide sequencing via tandem mass spectrometry. *J Comput Biol* 1999, 6, 327-342.

Chen, T.; Kao, M.; Tepel, M.; Rush, J.; Church, G. A dynamic programming approach to de novo peptide sequencing via tandem mass spectrometry. *J Comput Biol* 2001, 8, 325-337.

Frank, A.; Pevzner, P. PepNovo: De Novo Peptide Sequencing via Probabilistic Network Modeling. *Analytical Chemistry* 2005, 77, 964-973.

Bafna, V.; Edwards, N. On de-novo interpretation of tandem mass spectra for peptide identification. *Proceedings of the Seventh Annual International Conference on Computational Molecular Biology* 2003, pages 9-18.

Lu, B.; Chen, T. A suboptimal algorithm for de novo peptide sequencing via tandem mass spectrometry. *J Comput Biol* 2003, 10, 1-12.

Ma, B.; Zhang, K.; Hendrie, C.; Liang, C.; Li, M.; Doherty-Kirby, A.; Lajoie, G. PEAKS: powerful software for peptide de novo sequencing by tandem mass spectrometry. *Rapid Commun Mass Spectrom* 2003, 17, 2337-2342.

Bern, M.; Goldberg, D. De novo analysis of peptide tandem mass spectra by spectral graph partitioning. *Journal of Computational Biology* 2006, 13, 364-78.

Fischer, B.; Roth, V.; Roos, F.; Grossmann, J.; Baginsky, S.; Widmayer, P.; Gruissem, W.; Buhmann, J. NovoHMM: A Hidden Markov Model for de Novo Peptide Sequencing. *Anal. Chem.* 2005, 77, 7265-7273.

Grossmann, J.; Roos, F.; Cieliebak, M.; Liptak, Z.; Mathis, L.; Muller, M.; Gruissem, W.; Baginsky, S. AUDENS: a tool for automated peptide de novo sequencing. *J. Proteome Res* 2005, 4, 1768-1774.

Dimaggio Jr, P.; Floudas, C. De Novo Peptide Identification via Tandem Mass Spectrometry and Integer Linear Optimization. *Anal Chem* 2007, 79, 1433-1446.

Mo, L.; Dutta, D.; Wan, Y. Msnovo: a dynamic programming algorithm for de novo peptide sequencing via tandem mass spectrometry. *Anal. Chem* 2007, 79, 4870-4878.

Dewey, T. A sequence alignment algorithm with an arbitrary gap penalty function. *J Comput Biol* 2001, 8, 177-90.

Frank, A.; Tanner, S.; Bafna, V.; Pevzner, P. Peptide sequence tags for fast database search in mass-spectrometry. *J. Proteome Res* 2005, 4, 1287-1295.

Tabb, D.; Fernando, C.; Chambers, M. Myrimatch: highly accurate tandem mass spectral peptide identification by multivariate hypergeometric analysis. *J. Proteome Res.* 2007, 6, 654-661.

Bern, M.; Cai, Y.; Goldberg, D. Lookup peaks: a hybrid of de novo sequencing and database search for protein identification by tandem mass spectrometry. *Anal Chem* 2007, 79, 1393-1400.

Shilov, I.; Seymour, S.; Patel, A.; Loboda, A.; Tang, W.; Keating, S.; Hunter, C.; Nuwaysir, L.; Schaeffer, D. The paragon algorithm, a next generation search engine that uses sequence temperature values and feature probabilities to identify peptides from tandem mass spectra. *Mol Cell Proteomics.* 2007, 6, 1638-1655.

Gupta, N.; Tanner, S.; Jaitly, N.; Adkins, J.; Lipton, M.; Edwards, R.; Romine, M.; Osterman, A.; Bafna, V.; Smith, R.; Pevzner, P. Whole proteome analysis of post-translational modifications: applications of mass-spectrometry for proteogenomic annotation. *Genome Res.* 2007, 17, 1362-1377.

Craig, R.; Beavis, R. TANDEM: matching proteins with tandem mass-spectra. *Bioinformatics* 2004, 20, 1466-1467.

Nesvizhskii, A.; Keller, A.; Kolker, E.; Aebersold, R. A statistical model for identifying proteins by tandem mass spectrometry. *Anal. Chem.* 2003, 75, 4646-4658.

Tabb, D.; McDonald, W.; Yates, J. Dtaselect and contrast: tools for assembling and comparing protein identifications from shotgun proteomics. *J. Proteome Res.* 2002, 1, 21-26.

Zhang, B.; Chambers, M.; Tabb, D. Proteomic Parsimony through Bipartite Graph Analysis Improves Accuracy and Transparency. *J. Proteome Res* 2007, 6, 3549-3557.

Gupta, N.; Benhamida, J.; Bhargava, D.; Goodman, E.; Kain, I.; Nguyen, N.; Ollikainen, N.; Rodriguez, J.; Wang, J.; Lipton, M.; Romine, M.; Bafna, V.; Smith, R.; Pevzner, P. Comparative Proteogenomics: Combining Mass Spectrometry and Comparative Genomics to Analyze Multiple Genomes. *Genome Res.,* 2008 (in press).

Wan, Y.; Yang, A.; Chen, T. PepHMM: A Hidden Markov Model Based Scoring Function for Mass Spectrometry Database Search. *Anal Chem* 2006, 78, 432-7.

Venable, J.; Yates 3rd, J. Impact of ion trap tandem mass spectra variability on the identification of peptides. *Anal Chem* 2004, 76, 2928-37.

Alves, G.; Yu, Y. Robust accurate identification of peptides (RAId): deciphering MS2 data using a structured library search with de novo based statistics. *Bioinformatics* 2005, 21, 3726-3732.

Frank, A.; Savitski, M.; Nielsen, M.; Zubarev, R.; Pevzner, P. De novo Peptide sequencing and identification with precision mass spectrometry. *J Proteome Res* 2007, 6, 114-23.

Hansen, B.; Davey, S.; Ham, A.; Liebler, D. P-Mod: an algorithm and software to map modifications to peptide sequences using tandem MS data. *J Proteome Res* 2005, 4, 358-68.

Searle, B.; Dasari, S.; Turner, M.; Reddy, A.; Choi, D.; Wilmarth, P.; McCormack, A.; David, L.; Nagalla, S. High-throughput identification of proteins and unanticipated sequence modifications using a mass-based alignment algorithm for MS/MS de novo sequencing results. *Anal. Chem* 2004, 76, 2220-2230.

Bartels, C., Fast algorithm for peptide sequencing by mass spectroscopy. *Biomed. Environ. Mass Spectrom.* 1990, 19, 363-368.

The invention claimed is:

1. A method for identifying peptides using tandem mass spectrometry, comprising:

obtaining an experimental spectrum for a peptide to be analyzed, the experimental spectrum comprising a plurality of fragment peaks and having a parent mass, each fragment peak corresponding to a mass within the experimental spectrum;

using a scoring function, scoring a match between the experimental spectrum and a spectrum corresponding to each candidate peptide of a plurality of candidate peptides to generate a match score for each candidate peptide, wherein the scoring function has a value corresponding to a number of fragment peaks in the experimental spectrum matching fragment peaks in a spectrum of the candidate peptide;

using the match scores, computing, using a computer comprising a processor and a memory, a generating function of the experimental spectrum to determine a number of candidate peptides at each value of the scoring function, wherein the generating function is determined according to the relationship:

$$\sum_{all\_peptides\_P} e^{-Energy(P,S)} = \sum_{t} x(t) \cdot e^{-t}$$

wherein Energy(P,S) is an energy score, x(t) is the number of peptides with energy t and S is the experimental spectrum;

determining a score distribution of match scores of all candidate peptides for the experimental spectrum;

using the score distribution, identifying a subset of the candidate peptides to be reported as possible explanations of the experimental spectrum; and generating a report for output to a display device or a memory device comprising a listing of the identified subset of candidate peptides and their score distributions.

2. The method of claim 1, further comprising:

determining an energy score for each pairing of the experimental spectrum and a candidate peptide, wherein the energy score comprises a difference between a match score of the pairing and a match score of a best matching candidate peptide.

3. The method of claim 2, wherein the match score of a best matching candidate peptide is estimated using a de novo sequencing algorithm to define a plurality of peptide reconstructions.

4. The method of claim 3, wherein the number of peptide reconstructions is counted for each energy score to determine a total number of peptide reconstructions to be reported for the experimental spectrum.

5. The method of claim 4, wherein the total number of peptide reconstructions is computed by summing all of the candidate peptides from the subset of candidate peptides for all mass values within a pre-determined window around the parent mass.

6. A method for identifying peptides using tandem mass spectrometry, comprising:
    obtaining an experimental spectrum for a peptide to be analyzed, the experimental spectrum comprising a plurality of fragment peaks and having a parent mass, each fragment peak corresponding to a mass within the experimental spectrum;
    using a scoring function, scoring a match between the experimental spectrum and a spectrum corresponding to each candidate peptide of a plurality of candidate peptides to generate a match score for each candidate peptide, wherein the scoring function has a value corresponding to a number of fragment peaks in the experimental spectrum matching fragment peaks in a spectrum of the candidate peptide;
    using the match scores, computing, using a computer comprising a processor and a memory, a generating function of the experimental spectrum to determine a number of candidate peptides at each value of the scoring function, wherein the generating function is a weighted generating function and further comprising determining a probability of a peptide having a given match score, and wherein the weighted generating function is determined according to the relationship:

$$\sum_{all\ peptides\ P} \mathrm{prob}(P) \cdot e^{-Energy(P,S)} = \sum_t y(t) \cdot e^{-t},$$

wherein Energy(P,S) is an energy score, y(t) is the overall probability of all peptides with energy t and S is the experimental spectrum;
    determining a score distribution of match scores of all candidate peptides for the experimental spectrum;
    using the score distribution, identifying a subset of the candidate peptides to be reported as possible explanations of the experimental spectrum; and
    generating a report for output to a display device or a memory device comprising a listing of the identified subset of candidate peptides and their score distributions.

7. The method of claim 6, wherein the spectral probability comprises a total probability of all peptides with scores equal to or larger than the given match score.

* * * * *

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 1

Gly Ala Ile Asp Lys Ala Glu Glu Ile Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 2

Gln Pro Met Gly Ala Glu Ala Glu Leu Arg
1               5                   10

<210> SEQ ID NO 3
<211> LENGTH: 9
<212> TYPE: PRT
<213> ORGANISM: Artificial Sequence
<220> FEATURE:
```

-continued

```
<223> OTHER INFORMATION: de novo peptide sequence reconstruction from
      MS/MS spectra

<400> SEQUENCE: 3

Asp Gln Glu Leu Leu Ser Glu Ile Arg
1               5

<210> SEQ ID NO 4
<211> LENGTH: 9
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 4

Gln Ile Asp Lys Ala Glu Glu Ile Arg
1               5

<210> SEQ ID NO 5
<211> LENGTH: 10
<212> TYPE: PRT
<213> ORGANISM: Artificial Sequence
<220> FEATURE:
<223> OTHER INFORMATION: de novo peptide reconstruction from MS/MS
      spectra

<400> SEQUENCE: 5

Gln Ile Asp Gly Ala Ala Glu Glu Ile Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 6

Ile Arg Ser Ile Glu Ser Gln Lys Arg
1               5
```